United States Patent
De Boer et al.

(10) Patent No.: US 9,605,255 B2
(45) Date of Patent: Mar. 28, 2017

(54) OLIGONUCLEOTIDES FOR MAKING A CHANGE IN THE SEQUENCE OF A TARGET RNA MOLECULE PRESENT IN A LIVING CELL

(71) Applicant: ProQR Therapeutics II B.V., Leiden (NL)

(72) Inventors: Daniel Anton De Boer, Putten (NL); Tita Ritsema, Utrecht (NL)

(73) Assignee: ProQR Therapeutics II B.V., Leiden (NL)

(*) Notice: Subject to any disclaimer, the term of this patent is extended or adjusted under 35 U.S.C. 154(b) by 0 days.

(21) Appl. No.: 14/414,303

(22) PCT Filed: Jul. 12, 2013

(86) PCT No.: PCT/NL2013/050534
§ 371 (c)(1),
(2) Date: Jan. 12, 2015

(87) PCT Pub. No.: WO2014/011053
PCT Pub. Date: Jan. 16, 2014

(65) Prior Publication Data
US 2015/0197744 A1  Jul. 16, 2015

Related U.S. Application Data

(60) Provisional application No. 61/670,681, filed on Jul. 12, 2012, provisional application No. 61/718,801, filed on Oct. 26, 2012.

(30) Foreign Application Priority Data

May 3, 2013 (EP) .................................... 13166465
Jun. 18, 2013 (EP) .................................... 13172515
Jun. 26, 2013 (EP) .................................... 13173818

(51) Int. Cl.
| | |
|---|---|
| C12N 15/01 | (2006.01) |
| C12N 15/11 | (2006.01) |
| A61K 31/7088 | (2006.01) |
| A61K 38/46 | (2006.01) |

(52) U.S. Cl.
CPC .......... *C12N 15/01* (2013.01); *A61K 31/7088* (2013.01); *A61K 38/465* (2013.01); *C12N 15/111* (2013.01); *C12N 2310/11* (2013.01); *C12N 2320/34* (2013.01)

(58) Field of Classification Search
None
See application file for complete search history.

(56) References Cited

U.S. PATENT DOCUMENTS

| | | | |
|---|---|---|---|
| 6,165,782 A | 12/2000 | Naldini et al. | |
| 6,207,455 B1 | 3/2001 | Chang | |
| 6,218,181 B1 | 4/2001 | Verma et al. | |
| 6,277,633 B1 | 8/2001 | Olsen | |
| 6,323,031 B1 | 11/2001 | Cichutek | |
| 8,314,226 B2* | 11/2012 | Tabatadze ............ | C12N 15/102 536/24.33 |
| 2011/0263681 A1* | 10/2011 | De Fougerolles . | C12N 15/1138 514/44 A |
| 2015/0209448 A1 | 7/2015 | de Boer et al. | |

FOREIGN PATENT DOCUMENTS

| | | |
|---|---|---|
| WO | WO-94/26887 A1 | 11/1994 |
| WO | WO-2005/094370 A2 | 10/2005 |
| WO | WO-2010/012472 A1 | 2/2010 |
| WO | WO-2011/097641 A1 | 8/2011 |
| WO | WO-2011/150408 A2 | 12/2011 |
| WO | WO-2014/011050 A1 | 1/2014 |
| WO | WO-2014/011053 A1 | 1/2014 |

OTHER PUBLICATIONS

Lorain et al. (2010) Exon Exchange Approach to Repair Duchenne Dystrophin Transcripts. PLoS ONE, 5(5):e10894, pp. 1-11.*
Alibakhshi et al. (2008) Analysis of the CFTR gene in Iranian cystic fibrosis patients: Identification of eight novel mutations. Journal of Cystic Fibrosis, 7:102-109.*
Molenaar et al. (2001) Molenaar et al. (2001) Nucleic Acids Research, 29(17):e89, pp. 1-9. Nucleic Acids Research, 29(17):e89, pp. 1-9.*
Hegele, R. (2002) SNP Judgments and Freedom of Association. Arterioscler Thromb Vasc Biol, 22:1058-1061.*
Harris et al. (2007) Molecular identification of bacteria in bronchoalveolar lavage fluid from children with cystic fibrosis. PNAS, 104(51):20529-20533.*
Lai et al. (2009) Mucus-penetrating nanoparticles for drug and gene delivery to mucosal tissues. Advanced Drug Delivery Reviews, 61:158-171.*
Stern et al. (2000) A Comparison of the Efficacy and Tolerance of Pancrelipase and Placebo in the Treatment of Steatorrhea in Cystic Fibrosis Patients With Clinical Exocrine Pancreatic Insufficiency. The American Journal of Gastroenterology, 95(8):1932-1938.*
Donaldson et al. (2006) Mucus Clearance and Lung Function in Cystic Fibrosis with Hypertonic Saline. The New England Journal of Medicine, 354:241-250.*
Friedman et al. (1999) Correction of Aberrant Splicing of the Cystic Fibrosis Transmembrane Conductance Regulator (CFTR) Gene by Antisense Oligonucleotides. The Journal of Biological Chemistry, 274(51):36193-36199.*
Berger et al. (2016) "mRNA trans-splicing in gene therapy for genetic diseases," WIREs RNA doi: 10.1002/wrna.1347.
Edelstein et al. (2004) "Gene therapy clinical trials worldwide 1989-2004—an overview," J. Gene Med., 6: 597-602.
Ginn et al. (2013) "Gene therapy clinical trials worldwide to 2012—an update," J. Gene Med., 15: 65-77.

(Continued)

*Primary Examiner* — Neil P Hammell
(74) *Attorney, Agent, or Firm* — Goodwin Procter LLP

(57) ABSTRACT

The present invention relates to the field of gene therapy, more specifically to oligonucleotides for making a change in the sequence of a target RNA molecule present in a living cell.

32 Claims, 12 Drawing Sheets

(56) References Cited

OTHER PUBLICATIONS

Figures 3, 4:
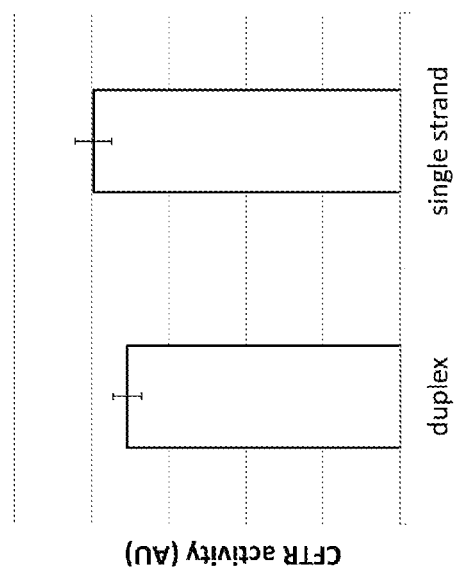

Lander et al. (1994) "Genetic dissection of complex traits," Science, 265: 2037-2048.
Sierakowska et al. (1996) "Repair of thalassemic human β-globin mRNA in mammalian cells by antisense oligonucleotides," Proc. Natl. Acad. Sci. USA, 93: 12840-12844.
Verma et al. (2005) "Gene Therapy: Twenty-first century medicine," Annu. Rev. Biochem., 74: 711-738.
Amado et al. (1999) "Lentiviral Vectors—the Promise of Gene Therapy Within Reach?" Science, 285: 674-6 (commentary piece, online text).
Anderson (1998) "Human gene therapy," Nature, 392: 25-30.
Bertoni, C. et al. (2009) "Enhanced gene repair mediated by methyl-CpG-modified single-stranded oligonucleotides," Nucleic Acids Research, 37(22): 7468-7482.
Chao H. et al. (2003) "Phenotype correction of hemophilia A mice by spliceosome-mediated RNA trans-splicing," Nat. Med., 9(8): 1015-1019.
Coady T.H. et al. (2008) "Development of a single vector system that enhances trans-splicing of SMN2 transcripts," PLoS One, 3(10):e3468.
Dallinger G. et al. (2003) "Development of spliceosome-mediated RNA transsplicing (SMaRT™) for the correction of inherited skin diseases," Experimental Dermatology, 12: 37-46.
De Piedoue, G. et al. (2007) "Targeted Gene Correction with 5' Acridine-Oligonucleotide Conjugates," Oligonucleotides, 17(2): 258-263.
Disterer, P. et al. (2012) "Oligonucleotide-mediated gene editing is underestimated in cells expressing mutated green fluorescent protein and is positively associated with target protein expression," J. Gene Med., 14(2): 109-119.
Engstrom, J. et al. (2009) "Regulation of targeted gene repair by intrinsic cellular processes," BioEssays, 31(2): 159-168.
Federico (1999) "Lentiviruses as gene delivery vectors," Curr. Opin. Biotechnol., 10: 448-53.
Goncalves (2005) "Adeno-associated virus: from defective virus to effective vector," Virol. J., 2(1): 43.
Goncz, K.K. et al. (2001) "Expression of ΔF508 CFTR in normal mouse lung after site-specific modification of CFTR sequences by SFHR," Gene Therapy, 8(12): 961-965.
Horiuchi T. et al. (2006) "Alternative trans-splicing: a novel mode of pre-mRNA processing," Biol. Cell., 98(2): 135-40.
Igoucheva, O. et al. (2001) "Targeted gene correction by small single-stranded oligonucleotides in mammalian cells," Gene Therapy, 8(5): 391-399.
Igoucheva, O. et al. (2008) "Oligonucleotide-Mediated Gene Targeting in Human Hepatocytes: Implications of Mismatch Repair," Oligonucleotides, 18(2): 111-122.
International Preliminary Report on Patentability for International Patent Application No. PCT/NL2013/050531, dated Jan. 13, 2015 (7 pages).
International Preliminary Report on Patentability for International Patent Application No. PCT/NL2013/050534, dated Jun. 13, 2014 (13 pages).
International Search Report and Written Opinion for International Patent Application No. PCT/NL2013/050531, mailed on Nov. 25, 2013 (12 pages).
International Search Report and Written Opinion for International Patent Application No. PCT/NL2013/050534, mailed on Dec. 3, 2013 (15 pages).
Kay et al. (2001) "Viral vectors for gene therapy: the art of turning infectious agents into vehicles of therapeutics," Nat. Med., 7: 33-40.
Knauert et al. (2001) "Triplex forming oligonucleotides: sequence-specific tools for gene targeting," Hum. Mol. Genet., 10: 2243-2251.
Koller, U. et al. (2011) "A novel screening system improves genetic correction by internal exon replacement," Nucleic Acids Research, 39(16): 1-11.
Kormann M.S. et al. (2011) "Expression of therapeutic proteins after delivery of chemically modified mRNA in mice," Nat. Biotechnol. 29(2): 154-157.

Liu, X. et al. (2005) "Spliceosome-Mediated RNA Trans-Splicing with Recombinant Adena-Associated Virus Partially Restores Cystic Fibrosis Transmembrane Conductance Regulator Function to Polarized Human Cystic Fibrosis Airway Epithelial Cells," Human Gene Therapy, 16: 1116-1123.
Livingston, P. et al. (2012) "Oligonucleotide Delivery by Nucleofection Does Not Rescue the Reduced Proliferation Phenotype of Gene-Edited Cells," Nucleic Acid Therapeutics, 22(6): 405-413.
Lorain S. et al. (2010) "Exon Exchange Approach to Repair Duchenne Dystrophin Transcripts, " PLoS One 5(5): e10894.
Marin et al. (1997) "Towards efficient cell targeting by recombinant retroviruses," Mol. Med. Today 3: 396-403.
McLachlan, J. et al. (2009) "Specific targeted gene repair using single-stranded DNA oligonucleotides at an endogenous locus in mammalian cells uses homologous recombination," DNA Repair, 8(12): 1424-1433.
Papaioannou, I. et al. (2009) "Use of internally nuclease-protected single-strand DNA oligonucleotides and silencing of the mismatch repair protein, MSH2, enhances the replication of corrected cells following gene editing," J. Gene Med., 11(3): 267-274.
Papaioannou, I. et al. (2012) "Oligonucleotide-directed gene-editing technology: mechanisms and future prospects," Expert Opin. Biol. Ther., 12(3): 329-342.
Peacock H. et al. (2011) "Nucleobase and Ribose Modifications Control Immunostimulation by a MicroRNA-122-mimetic RNA," J. Am. Chem. Soc., 133: 9200-9203.
Peng et al. (1999) "Viral vector targeting," Curr. Opin. Biotechnol., 10: 454-7.
Reiser (2000) "Production and concentration of pseudotyped HIV-1-based gene transfer vectors," Gene Ther., 7: 910-913.
Richardson et al. (2002) "Strategies for Hepatic Gene Correction," Drug Target, 10: 133-141.
Russell (2000) "Update on adenovirus and its vectors," J. Gen. Virol., 81: 2573-2604.
Shen, Y. et al. (2011) "RNA-driven genetic changes in bacteria and in human cells," Mutation Research, 717(1): 91-98.
Sommerfelt (1999) "Retrovirus receptors," J. Gen. Virol., 80: 3049-3064.
Song, Y. et al. (2009) "Functional Cystic Fibrosis Transmembrane Conductance Regulator Expression in Cystic Fibrosis Airway Epithelial Cells by AAV6.2-Mediated Segmental Trans-Splicing," Human Gene Therapy, 20: 267-281.
Tahara M. et al. (2004) "Trans-splicing repair of CD40 ligand deficiency results in naturally regulated correction of a mouse model of hyper-IgM Xlinked immunodeficiency," Nat. Med., 10(8): 835-841.
Thorpe P. et al. (2002) "Optimising gene repair strategies in cell culture," Gene Therapy, 9(11): 700-702.
Thoung et al. (1993) "Sequence-Specific Recognition and Modification of Double-Helical DNA by Oligonucleotides," Angewandte Chemie. Intl. Ed. Eng., 32, 666-690.
Vigna et al. (2000) "Lentiviral vectors: excellent tools for experimental gene transfer and promising candidates for gene therapy," J. Gene Med., 2: 308-316.
Wally V. et al. (2012) "Spliceosome-Mediated Trans-Splicing: The Therapeutic Cut and Paste," J. Invest. Dermatol., 132(8): 1959-1966.
Walther et al. (2000) "Viral Vectors of Gene Transfer. A Review of Their Use in the Treatment of Human Diseases," Drugs, 60: 249-271.
Zamecnik, P. et al. (2004) "Reversal of cystic fibrosis phenotype in a cultured Δ508 cystic fibrosis transmembrane conductance regulator cell line by oligonucleotide insertion," PNAS, 101(21): 8150-8155.
Kolb et al. (2005) "Site-directed genome modification: nucleic acid and protein modules for targeted integration and gene correction," Trends Biotechnol., 23(8): 399-406.
Search Report for Chinese Patent Application No. 201380047636.5 mailed on May 20, 2016 (English translation; 2 pages).
Wu (2006) "Study on the Action Mechanism of Single-stranded Oligonucleotide mediated Site-directed Gene Repair," Doctoral Dissertation.

(56) References Cited

OTHER PUBLICATIONS

Yang et al. (2007) "Study on correcting site mutations by specially designed oligonucleotide strands," Carcinogenesis, Teratogenesis & Mutagenesis, 19(1): 79-81.

* cited by examiner

Fig. 1

SEQ ID NO:5  WT   UAUGCCUGGCACCAUUAAAGAAAAAUAUCUUUGGUGUUUCCUAUGAUGAAUAUAGAUACAG

SEQ ID NO:6  Mut  UAUGCCUGGCACCAUUAAAGAAAAAUAUCAUUGGUGUUUCCUAUGAUGAAUAUAGAUACAG

Fig. 2

SEQ ID NO:7 Mut  UAUGCCUGGCACCAUUAAAGAAAAAUAUCAU     UGGUGUUUCCUAUGAUGAAUAUAGAUACAG   SEQ ID NO:8
SEQ ID NO:1                                    UUUCUUUUAUAGUAGAAACCACAAAGGAUACUA

SEQ ID NO:9  RS   UAUGCCUGGCACCAUUAAAGAAAAAUAUCAUCUUUGGUGUUUCCUAUGAUGAAUAUAGAUACAG

```
SEQ ID NO:10 WT    augccuggcaccauuaaagaaauauca ucuuuggug uuuccuagaugaauauagauac
SEQ ID NO:11        M  P  G  T  I  K  E  N  I  I  F  G  V  S  Y  D  E  Y  R  Y SEQ ID NO:12 Mut   augccuggcaccauuaaagaaauauca uuggug uuuccuagaugaauauagauac
SEQ ID NO:13        M  P  G  T  I  K  E  N  I  I  G  V  S  Y  D  E  Y  R  Y SEQ ID NO:14 RS    augccuggcaccauuaaagaaauauca ucuuuggug uuuccuagaugaauauagauac
SEQ ID NO:15        M  P  G  T  I  K  E  N  I  I  F  G  V  S  Y  D  E  Y  R  Y
```

Fig 7a

```
        5'-AUCAUAGGAAACACCAAAGAUGAUAUUUUCUUU-3'      oligonucleotide 010g;      SEQ ID NO:1

5'-ACCAUUAAAGAAAAUAUCAUUGGUGUUUCCUAUGAUGAAUAU-3'   Part of ΔF508 RNA;         SEQ ID NO:25
    T  I  K  E  N  I  I  G  V  S  Y  D  E  Y      Part of polypeptide(PP);   SEQ ID NO:26
                           ↓

3'-UUUCUUUUAUAGUAGAAACCACAAAGGAUACUA-5'     oligonucleotide 010g;      SEQ ID NO:1
5'-ACCAUUAAAGAAAAUAUCAUCUUUGGUGUUUCCUAUGAUGAAUAU-3' Part of WT RNA;           SEQ ID NO:27
    T  I  K  E  N  I  I  F  G  V  S  Y  D  E  Y   Part of WT PP;             SEQ ID NO:28
                          508
```

Fig 7b

```
        5'-AUCAUAGGAAACACCAAGAUGAUAUUUUCUUU-3'      oligonucleotide dF-ins2;  SEQ ID NO:16

5'-ACCAUUAAAGAAAAUAUCAUUGGUGUUUCCUAUGAUGAAUAU-3'   Part of ΔF508 RNA;         SEQ ID NO:25
    T  I  K  E  N  I  I  G  V  S  Y  D  E  Y      Part of PP;                SEQ ID NO:26
                           ↓

3'-UUUCUUUUAUAGUAGAACCACAAAGGAUACUA-5'      oligonucleotide dF-ins2;  SEQ ID NO:16
5'-ACCAUUAAAGAAAAUAUCAUCUUGGUGUUJCCUAUGAUGAAUAUA-3' Insertion of CU;          SEQ ID NO:29
    T  I  K  E  N  I  I  L  V  F  P  M  M  N  I   Frameshift in PP;          SEQ ID NO:30
                          508
```

Fig 7c

```
5'-AUCAUAGGAAACACCAGAUGAUAUUUUCUJU-3'    oligonucleotide dF-ins1; SEQ ID NO:17

5'-ACCAUUAAAGAAAAUAUCAUUGGUGUUUCCUAUGAUGAAUAU-3'  Part of AF508 RNA;   SEQ ID NO:25
    T  I  K  E  N  I  I  G  V  S  Y  D  E  Y      Part of PP;          SEQ ID NO:26
                         ↓

3'-UUUCUUUUAUAGUAGACCACAAAGGAUACJA-5'       oligonucleotide dF-ins1; SEQ ID NO:17
5'-ACCAUUAAAGAAAAUAUCAUCUGGUGUUUCCUAUGAUGAAUAU-3' Insertion of C;          SEQ ID NO:31
    T  I  K  E  N  I  I  W  C  F  L  -            Frameshift in PP;        SEQ ID NO:32
                        508
```

Fig 7d

```
5'-CAUCAUAGGAAACACCAGAUGAUAUUUUCUUUA-3'   oligonucleotide dF-ins1 33b; SEQ ID NO:18

5'-ACCAUUAAAGAAAAUAUCAUUGGUGUUUCCUAUGAUGAAUAU-3' Part of AF508 RNA;   SEQ ID NO:25
    T  I  K  E  N  I  I  G  V  S  Y  D  E  Y     Part of PP;          SEQ ID NO:26
                         ↓

3'-AUUUCUUUUAUAGUAGACCACAAAGGAUACUAC-5'   oligonucleotide dF-ins1 33b; SEQ ID NO:18

5'-ACCAUUAAAGAAAAUAUCAUCUGGUGUUUCCUAUGAUGAAUAU-3' Insertion of C;     SEQ ID NO:31
    T  I  K  E  N  I  I  W  C  F  L  -            Frameshift in PP;   SEQ ID NO:32
                        508
```

Fig 8a

```
5'-AUAGGAAACACCAAAUCAGAUGAUAUUUCUUU-3'    oligonucleotide CFTR WT X;   SEQ ID NO:19

5'-ACCAUUAAAGAAAAUAUCAUCUUUGGUGUUUCCUAUGAUGAAUAU-3'   Part of WT RNA;   SEQ ID NO:27
       T  I  K  E  N  I  I  F  G  V  S  Y  D  E  Y       Part of PP;       SEQ ID NO:28

↓

3'-UUUCUUUUAUAGUAGACUAAACCACAAAGGAUA-5'    oligonucleotide CFTR WT X;   SEQ ID NO:19
5'-ACCAUUAAAGAAAAUAUCAUCUGAUUGGUGUUUCCUAUGAUGAA-3'    Insertion of stop;   SEQ ID NO:34
   T  I  K  E  N  I  I  -                            Part of truncated PP;  SEQ ID NO:35
                     508
```

Fig 8b

```
5'-AUAGGAAACACCAAAUCGAUGAUAUUUCUUU-3'           oligonucleotide CFTR WT Ins2; SEQ ID NO:20

5'-ACCAUUAAAGAAAAUAUCAUCUUUGGUGUUUCCUAUGAUGAAUAU-3'   Part of WT RNA;   SEQ ID NO:27
       T  I  K  E  N  I  I  F  G  V  S  Y  D  E  Y       Part of PP;       SEQ ID NO:28

↓

3'-UUUCUUUUAUAGUAGCUAAACCACAAAGGAUA-5'      oligonucleotide CFTR WT Ins2; SEQ ID NO:20
5'-ACCAUUAAAGAAAAUAUCAUCGAUUGGUGUUUCCUAUGAUGAAU-3'    Insertion of GA;      SEQ ID NO:36
   T  I  K  E  N  I  I  D  L  V  F  P  M  M  N       Frameshift in PP;     SEQ ID NO:37
                     508
```

Fig 8c

```
5'-AUAGGAAACACCAAAUGAUGAUAUUUCUUU-3'         oligonucleotide CFTR WT Ins1;  SEQ ID NO:21

5'-ACCAUUAAAGAAAAUAUCAUCUUUGGUGUUUCCUAUGAUGAAUAU-3'   Part of WT RNA;    SEQ ID NO:27
        T  I  K  E  N  I  I  F  G  V  S  Y  D  E  Y      Part of PP;        SEQ ID NO:28

↓

3'-UUUCUUUAUAGUAGUAAACCACAAAGGAUA-5'          oligonucleotide CFTR WT Ins1;  SEQ ID NO:21
5'-ACCAUUAAAGAAAAUAUCAUCAUUUGGUGUUUCCUAUGAUGAAUA-3'      Insertion of A;        SEQ ID NO:38
    T  I  K  E  N  I  I  I  W  C  F  L  -              Frameshift and stop in PP;  SEQ ID NO:39
                        508
```

Fig 8d

```
5'-AUAGGAAACACCAAAGAGGAUGAUAUUUJCUUU-3'        oligonucleotide CFTR WT L;    SEQ ID NO:22

5'-ACCAUUAAAGAAAAUAUCAUCUUUGGUGUUUCCUAUGAUGAAUAU-3'   Part of WT RNA;    SEQ ID NO:27
        T  I  K  E  N  I  I  F  G  V  S  Y  D  E  Y      Part of PP;        SEQ ID NO:28

↓

3'-UUUCUUUAUAGUAGGAGAAACCACAAAGGAUA-5'         oligonucleotide CFTR WT L;    SEQ ID NO:22
5'-ACCAUUAAAGAAAAUAUCAUCCUCUUUGGUGUUUCCUAUGAUGAA-3'     Insertion of CUC;      SEQ ID NO:41
    T  I  K  E  N  I  I  L  F  G  V  S  Y  D  E       Insertion of leucine at 508;  SEQ ID NO:42
                        508
```

Fig 8e

```
5'-AGGCAUAAUCCAGGCAUCAAAACUGAGAACAGAA-3'     oligonucleotide CFTR WT OX;   SEQ ID NO:23

5'-AUUUCAUUCUGUUCUCAGUUUUCCUGGAUUAUGCCUGGCACCAUU-3'   Part of WT RNA;  SEQ ID NO:43
         I  S  F  C  S  Q  F  S  W  I  M  P  G  T  I      Part of PP;      SEQ ID NO:44

↓

3'-AAGACAAGAGUCAAAACUAGGACCUAAUACGGA-5'    oligonucleotide CFTR WT OX;  SEQ ID NO:23
5'-AUUUCAUUCUGUUCUCAGUUUUGAUCCUGGAUUAUGCCUGGCACC-3'  Insertion of stop;        SEQ ID NO:45
    I  S  F  C  S  Q  F  -                          Part of truncated PP;      SEQ ID NO:46
                        495
```

Fig 8f

```
5'-AUGGUGCCAGGCAUAAGGAUCCAGGAAAACUGA-3'       oligonucleotide CFTR WT OL;    SEQ ID NO:24

5'-UUCUGUUCUCAGUUUUCCUGGAUUAUGCCUGGCACCAUUAAAGAAAAU-3'   Part of WT RNA;  SEQ ID NO:47
         F  C  S  Q  F  S  W  I  M  P  G  T  I  K  E  X     Part of PP;      SEQ ID NO:48

↓

3'-AGUCAAAAGGACCUAGGAAUACGGACCGUGGUA-5'   oligonucleotide CFTR WT OL;  SEQ ID NO:24
5'-UUCUGUUCUCAGUUUUCCUGGAUCCUUAUGCCUGGCACCAUUAAAGAA-3'  Insertion of CCU;    SEQ ID NO:49
     F  C  S  Q  F  S  W  I  L  M  P  G  T  I  K  E    Insertion of leucine at 498; SEQ ID NO:50
                        498
```

Fig. 9d

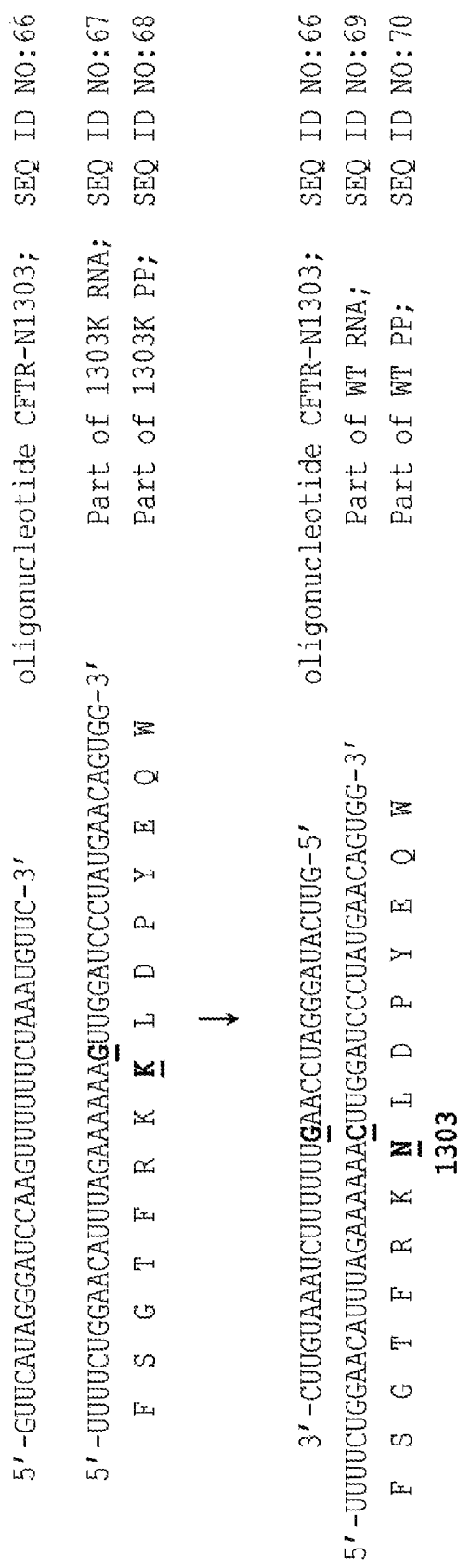

```
5'-GUUCAUAGGGAUCCAAGUUUUUCUAAAUGUUC-3'      oligonucleotide CFTR-N1303;   SEQ ID NO:66

5'-UUUUCUGGAACAUUUAGAAAAAGUUGGAUCCCUAGAACAGUGG-3'   Part of 1303K RNA;    SEQ ID NO:67
    F  S  G  T  F  R  K  K  L  D  P  Y  E  Q  W      Part of 1303K PP;    SEQ ID NO:68
                         →

3'-CUUGUAAAUCUUUUUGAACCUAGGGAUAUACUUG-5'      oligonucleotide CFTR-N1303;   SEQ ID NO:66
5'-UUUUCUGGAACAUUUAGAAAAACUUGGAUCCCUAGAACAGUGG-3'   Part of WT RNA;        SEQ ID NO:69
    F  S  G  T  F  R  K  N  L  D  P  Y  E  Q  W      Part of WT PP;         SEQ ID NO:70
                      1303
```

OLIGONUCLEOTIDES FOR MAKING A CHANGE IN THE SEQUENCE OF A TARGET RNA MOLECULE PRESENT IN A LIVING CELL

RELATED APPLICATIONS

This application is the U.S. national stage of International (PCT) Patent Application PCT/NL2013/050534, filed Jul. 12, 2013, which claims priority to U.S. Provisional Application No. 61/670,681, filed Jul. 12, 2012; U.S. Provisional Application No. 61/718,801, filed Oct. 26, 2012; European Patent Application No. 13166465.8, filed May 3, 2013; European Patent Application No. 13172515.2, filed Jun. 18, 2013; and European Patent Application No. 13173818.9, filed Jun. 26, 2013.

FIELD OF THE INVENTION

The present invention relates to the field of gene therapy, more specifically to oligonucleotides for making a change in the sequence of a target RNA molecule present in a living cell.

BACKGROUND OF THE INVENTION

Numerous genetic diseases are caused by mutations in the genome. Several types of modifications have been found to be mutated in the genome: deletion of one or several base pairs, one or several mismatches in the sequence of the gene, insertion of one or several nucleotides, or repeat triplet reiteration and absence or duplication of a whole or part of a gene.

Genetic diseases caused by mismatches, deletion or insertion of one or several base pairs include cystic fibrosis, muscular dystrophy, sickle cell anemia, hemophilia, β-thalassemia, Fragile X syndrome.

RNA repair can be employed to repair genetic defects at the RNA level.

Oligonucleotides and complexes thereof have been employed as therapeutic molecules to repair DNA modifications (I Papaioannou, J P Simons, J S Owen Oligonucleotide-directed gene-editing technology: mechanisms and future prospects Expert Opin. Biol. Ther. (2012) 12(3):329-342). These oligomers can contain RNA and/or DNA nucleotides, or modified RNA or DNA nucleotides. They are employed to obtain site-specific repair of defective DNA. The repair was anticipated to occur through activation of endogenous DNA repair mechanisms after recognition of the introduced mismatch.

Triplex forming oligonucleotides also have been employed as sequence-specific tools for gene targeting. Triplex forming oligonucleotides bind in the major groove of double stranded DNA, with high affinity. Because of this characteristic, triplex forming oligonucleotides have been proposed as tools for the site specific corrections of targeted genes (Knauert et al., Hum Mol Genet. (2001) 10, 2243-2251; Richardson et al, Drug Target (2002) 10, 133-134; Thoung et al., (1993) Angewandte Chemie. Intl. Ed. Eng., 32, 666-690.). Current targeted gene repair methods are not very efficient, and/or have not been proven to work in living cells in situ, leaving space for another mechanism to repair gene defects.

Repair of defective genes at the RNA level has been reported. The specific repair of mRNA by a complex of duplexed oligonucleotides was e.g. employed to insert nucleotides in the ΔF508 CFTR mRNA in vitro. The mechanism through which this is mediated is postulated to be RNAse H-mediated degradation, followed by RNA repair. (P C Zamecnik, M K Raychowdhury, D R Tabatadze, H F Cantiello Reversal of cystic fibrosis phenotype in a cultured ΔF508 cystic fibrosis transmembrane conductance regulator cell line by oligonucleotide insertion Proc Natl Acad Sci 2004 101(21) 8150-8155; WO2005094370, oligonucleotide complex compositions and methods of use as gene alteration tools).

DESCRIPTION OF THE INVENTION

The present invention is directed to a method for targeted gene repair in living cells, more preferably in living cells in a multicellular organism (in vivo). The invention more specifically concerns making changes in a target RNA in living cells in vivo in multicellular organisms, more in particular in animals, more in particular mammals, even more specifically in humans. Despite earlier reports of gene repair in living cells, it is believed that this invention for the first time discloses the possibility to make changes in a target RNA molecule in a living cell in vivo, thereby changing the phenotype of that organism, using oligonucleotides, preferably single stranded oligonucleotides, more preferably single stranded oligoribonucleotides, even more specifically chemically modified single stranded oligoribonucleotides. Surprisingly, the oligonucleotides according to the invention can be administered in vivo without loss of activity and in such quantities as to substantially restore the diseased phenotype of the subject organism. The invention is illustrated through the administration into the lung of an organism suffering from cystic fibrosis of a chemically modified oligoribonucleotide that is capable of restoring the RNA sequence coding for CFTR, thereby restoring CFTR protein function and restoring CF phenotype, or at least ameliorating the condition, of the organism. Hence, this invention relates to an oligonucleotide, preferably a single strand antisense oligonucleotide; a composition comprising such oligonucleotide; a pharmaceutical composition comprising such oligonucleotide and a pharmaceutically acceptable carrier; use and methods of such oligonucleotide or composition for in vivo or in vitro RNA repair and/or making a change in the sequence of a target RNA molecule; such oligonucleotide or composition for use in the treatment or prevention of a disease related to a (genetic) disorder or related to a genetic mutation, comprising administration of such oligonucleotide or composition to a subject, preferably a human subject; and to a method for treatment or prevention of a disease related to a (genetic) disorder or related to a genetic mutation, comprising administration of such oligonucleotide or composition to a subject, preferably a human subject. Upon introduction of such, preferably single strand antisense, oligonucleotide in a cell, preferably a mammalian cell, more preferably a human cell, it is directed to the RNA or a precursor or a template thereof at the place where RNA needs to be repaired and possibly acts as a guide strand for RNA repair. The specific mechanism of repair is unknown, but the oligonucleotide according to the invention, preferably a single strand repair molecule preferably does not allow a role for RNAse H in the repair process. The change mediated in the target RNA could be directly on the RNA level or indirectly via DNA which is subsequently transcribed into the RNA molecule, or a precursor thereof. The oligonucleotides described herein are generally referred to as the oligonucleotide according to the invention and can be used in all embodiments of the present invention.

All embodiments of the present invention can be performed (in case of a method or use), or can be used (in case of a compound or composition) in vitro, in vivo, or ex vivo.

The present invention can conveniently be used for the treatment of cystic fibrosis, preferably by repair of the deltaF508 mutation in exon 10 of CFTR (cystic fibrosis transmembrane conductance regulator). The mode of action of an exemplary oligonucleotide according to the invention, the molecule depicted in SEQ ID NO: 1, is depicted in FIGS. 1-3 and 7A. The activity of an exemplary oligonucleotide according to the invention, the molecule depicted in SEQ ID NO: 1 compared to the previously described duplex (Zamecnik et al, supra), is illustrated in FIG. 4. The figure shows that the currently described single strand antisense oligonucleotide (AON) is as least as active as, and appears to be more active, in repairing CFTR compared to the previously described duplex molecule (P C Zamecnik, M K Raychowdhury, D R Tabatadze, H F Cantiello Reversal of cystic fibrosis phenotype in a cultured ΔF508 cystic fibrosis transmembrane conductance regulator cell line by oligonucleotide insertion Proc Natl Acad Sci 2004 101(21) 8150-8155; WO2005094370, oligonucleotide complex compositions and methods of use as gene alteration tools). The activity of SEQ ID NO: 1 was determined using the comparative assay as described in Zamecnik et al, supra, see inter alia FIG. 4 on page 8153.

The present invention can also conveniently be used for making a change in another target RNA molecule and/or the treatment of other diseases related to (genetic) disorders, such as but not limited to albinism, alpha-1-antitrypsin deficiency, Alzheimer disease, Amyotrophic lateral sclerosis, Asthma, β-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidormylosis bullosa, Fabry disease, Familial Adenomatous, Polyposis, Galactosemia, Gaucher's Disease, Glucose-6-phosphate dehydrogenase, Haemophilia, Hereditary Hematochromatosis, Hunter Syndrome, Huntington's disease, Hurler Syndrome, Inflammatory Bowel Disease (IBD), Inherited polyagglutination syndrome, Lesch-Nyhan syndrome, Lynch, Marfan syndrome, Mucopolysaccharidosis, Muscular Dystrophy, Myotonic dystrophy types I and II, Niemann-Pick disease type A, B and C, NY-esol related cancer, Parkinson's disease, Peutz-Jeghers Syndrome, Phenylketonuria, Pompe's disease, Primary Ciliary Disease, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, X-linked immunodeficiency, various forms of cancer (e.g. BRCA1 and 2 linked breast cancer and ovarian cancer), and the like.

In accordance with one preferred embodiment of the invention, the change in the target RNA sequence comprises the insertion of one or more nucleotides into the target RNA. In a more preferred embodiment the insertion of one or more nucleotides leads to the insertion of at least one amino acid sequence in a polypeptide sequence encoded by the target RNA sequence. In accordance with a most preferred embodiment, the insertion of an amino acid sequence causes the encoded polypeptide to be restored to a normally functioning polypeptide in the multicellular organism. Accordingly, most preferred embodiments of the invention are those where the target RNA sequence in a multicellular organism is associated with a disorder caused by the malfunctioning of the target RNA sequence and the genetic disorder is selected from the group of disorders caused by target RNA sequences lacking one or more nucleotides compared to normally functioning target RNA sequences. Preferred according to the invention are those target RNA sequences that lack at least part of a codon, which is restored by making a change in the RNA sequence using an oligonucleotide according to the invention.

The present invention shows that RNA repair can be established in vivo upon systemic administration of an oligonucleotide according to the invention. Depending on the tissue or organ involved in the disorder, or more generally in which a change in a target RNA is to be accomplished, the mode of administration may be tailored to optimize delivery of the oligonucleotide according to the invention. For disorders of the lungs and other respiratory ailments, oligonucleotides according to the invention may conveniently be administered directly to the lungs, for example through inhalation. Alternatively, depending on the disorder and/or the target tissue, administration may take place topically (e.g. on the skin) or systemically, such as intradermally, subcutaneously, intramuscularly, intravenously, orally, rectally, intracranially and the like.

The oligonucleotides according to the invention can contain DNA- or RNA-nucleotides; there can be modified DNA- or RNA-nucleotides present to enhance stability as described elsewhere herein. The oligonucleotide according to the invention may e.g. comprise an inosine and/or may comprise modified nucleotides, preferably selected from the group consisting of a 2'-O-alkyl ribose, 2'-O-methyl ribose, 2'Fluoro ribose, phosphorothioate, methylphosphonate, PMO, 5-methyl-dC, 2-amino-dA, C5-pyrimidine. One such preferred example of a stabilized nucleotide is a 2'-O-methyl modified nucleotide, another example is a Locked Nucleic Acid (LNA) nucleotide and/or a Peptide Nucleic Acid (PNA). Other measures to enhance stability could be for example phosphorothioate linkages between nucleotides. Oligonucleotides according to the invention can be prepared according to any method known in the art. The person skilled in the art knows how to synthesize the oligonucleotides according to the invention.

Accordingly, an oligonucleotide according to the invention is preferably chemically modified to resist endonucleases, exonucleases and RNaseH, and to promote (RNA) binding and duplex stability. The particular characteristics of a chosen chemistry at least in part affects the delivery of an oligonucleotide according to the invention to the target: administration route, biostability, biodistribution, intra-tissue distribution, and cellular uptake and trafficking. In addition, further optimization of oligonucleotide chemistry may be applied to enhance binding affinity and stability, enhance activity, improve safety, and/or to reduce cost of goods by reducing length or improving synthesis and/or purification procedures. Multiple chemical modifications are generally and/or commercially available to the person skilled in the art (such as 2'-O-methyl RNA and 5-substituted pyrimidines and 2,6-diaminopurines).

An oligonucleotide according to the invention may have at least one backbone, and/or sugar modification and/or at least one base modification.

A base modification includes a modified version of the natural purine and pyrimidine bases (e.g. adenine, uracil, guanine, cytosine, and thymine), such as hypoxanthine, orotic acid, agmatidine, lysidine, 2-thiopyrimidine (e.g. 2-thiouracil, 2-thiothymine), G-clamp and its derivatives, 5-substituted pyrimidine (e.g. 5-halouracil, 5-propynyluracil, 5-propynylcytosine, 5-aminomethyluracil, 5-hydroxymethyluracil, 5-aminomethylcytosine, 5-hydroxymethylcytosine, Super T), 7-deazaguanine, 7-deazaadenine, 7-aza-2,6-diaminopurine, 8-aza-7-deazaguanine, 8-aza-7-deazaadenine, 8-aza-7-deaza-2,6-diaminopurine, Super G, Super A, and N4-ethylcytosine, or derivatives thereof; $N^2$-cyclopentylguanine (cPent-G), $N^2$-cyclopentyl-2-aminopurine (cPent-AP), and $N^2$-propyl-2-aminopurine (Pr-AP), or derivatives thereof; and degenerate or universal bases, like 2,6-difluorotoluene or absent bases like abasic sites (e.g. 1-deoxyribose, 1,2-dideoxyribose, 1-deoxy-2-O-methylribose; or pyrrolidine derivatives in which the ring oxygen has been replaced with nitrogen (azaribose)). Examples of derivatives of Super A, Super G and Super T can be found in U.S. Pat. No. 6,683,173 (Epoch Biosciences), which is incorporated here entirely by reference. cPent-G, cPent-AP and Pr-AP were shown to reduce immunostimulatory effects when incorporated in siRNA (Peacock H. et al. *J. Am. Chem. Soc.* 2011, 133, 9200).

A sugar modification includes a modified version of the ribosyl moiety, such as 2'-O-modified RNA such as 2'-O-alkyl or 2'-O-(substituted)alkyl e.g. 2'-O-methyl, 2'-O-(2-cyanoethyl), 2'-O-(2-methoxyl)ethyl (2'-MOE), 2'-O-(2-thiomethyl)ethyl, 2'-O-butyryl, 2'-O-propargyl, 2'-O-allyl, 2'-O-(2-amino)propyl, 2'-O-(2-(dimethylamino)propyl), 2'-O-(2-amino)ethyl, 2'-O-(2-(dimethylamino)ethyl); 2'-deoxy (DNA); 2'-O-(haloalkoxy)methyl (Arai K. et al. *Bioorg. Med. Chem.* 2011, 21, 6285) e.g. 2'-O-(2-chloroethoxyl) methyl (MCEM), 2'-O-(2,2-dichloroethoxyl)methyl (DCEM); 2'-O-alkoxycarbonyl e.g. 2'-O-[2-(methoxycarbonyl)ethyl] (MOCE), 2'-O-[2-(N-methylcarbamoyl)ethyl] (MCE), 2'-O-[2-(N,N-dimethylcarbamoyl)ethyl] (DCME); 2'-halo e.g. 2'-F, FANA (2'-F arabinosyl nucleic acid); carbasugar and azasugar modifications; 3'-O-alkyl e.g. 3'-O-methyl, 3'-O-butyryl, 3'-O-propargyl; and their derivatives. Another modification includes "bridged" or "bicylic" nucleic acid (BNA), e.g. locked nucleic acid (LNA), xylo-LNA, α-L-LNA, β-D-LNA, cEt (2'-O,4'-C constrained ethyl) LNA, cMOEt (2'-O,4'-C constrained methoxyethyl) LNA, ethylene-bridged nucleic acid (ENA), tricyclo DNA; unlocked nucleic acid (UNA); cyclohexenyl nucleic acid (CeNA), altriol nucleic acid (ANA), hexitol nucleic acid (HNA), fluorinated HNA (F-HNA), pyranosyl-RNA (p-RNA), 3'-deoxypyranosyl-DNA (p-DNA); morpholino (PMO), cationic morpholino (PMOPlus), PMO-X; and their derivatives. It is also encompassed by the invention to introduce more than one distinct sugar modification in an oligonucleotide according to the invention. BNA derivatives are for example described in WO 2011/097641, which is incorporated in its entirety by reference. Examples of PMO-X are described in WO2011150408, which is incorporated here in its entirety by reference.

A backbone modification includes a modified version of the phosphodiester, such as phosphorothioate (PS), chirally pure phosphorothioate, phosphorodithioate (PS2), phosphonoacetate (PACE), phosphonoacetamide (PACA), thiophosphonoacetate, thiophosphonoacetamide, phosphorothioate prodrug, H-phosphonate, methyl phosphonate, methyl phosphonothioate, methyl phosphate, methyl phosphorothioate, ethyl phosphate, ethyl phosphorothioate, boranophosphate, boranophosphorothioate, methyl boranophosphate, methyl boranophosphorothioate, methyl boranophosphonate, methyl boranophosphonothioate, and their derivatives. Another modification includes phosphoramidite, phosphoramidate, N3'→P5' phosphoramidate, phosphordiamidate, phosphorothiodiamidate, sulfamate, dimethylenesulfoxide, sulfonate, triazole, oxalyl, carbamate, methyleneimino (MMI), and thioacetamido nucleic acid (TANA); and their derivatives. It is also encompassed by the invention to introduce more than one distinct backbone modification in an oligonucleotide according to the invention.

Other chemical modifications of an oligonucleotide according to the invention include peptide-base nucleic acid (PNA), boron-cluster modified PNA, pyrrolidine-based oxypeptide nucleic acid (POPNA), glycol- or glycerol-based nucleic acid (GNA), threose-based nucleic acid (TNA), acyclic threoninol-based nucleic acid (aTNA), morpholino-based oligonucleotide (PMO, PMO-X), cationic morpholino-based oligomers (PMOPlus), oligonucleotides with integrated bases and backbones (ONIBs), pyrrolidine-amide oligonucleotides (POMs) and their derivatives.

An oligonucleotide according to the invention contains a sequence complementary to the target RNA that is to be repaired and preferably encodes the wild-type polypeptide sequence. Accordingly, due to the degeneracy of codons, the oligonucleotide may comprise one or more degenerate complementary codons. The complementary nucleotides can be present on either side of the site that is to be repaired, i.e. the sequence flanking the sequence to be altered is preferably on the 3', 5' or both 3' and 5' side of the sequence to be altered. Upon basepairing of these complementary sequences the RNA repair is activated.

The sequence of the target RNA preferably differs from that of the repaired or wild type sequence. The non-repaired target RNA is preferably a mutated sequence. Preferably, the mutation is a substitution, deletion or insertion of a normal wild type sequence. The repaired targeted RNA is preferably a wild-type sequence of a gene or another desired reference sequence.

An oligonucleotide according to the invention preferably has a length of 15 to 100 nucleotides and is preferably at least 20, 21, 22, 23, 24, 25, 26, 27, 28, 29, 30, 31, 32, 33, 34, 35, 36, 37, 38, 39, or at least 40 nucleotides in length, of which at least 10 are complementary to the target RNA sequence. Some other nucleotides can be used as template (or inducer) for repair. Basepairing with the target mRNA sequence occurs preferentially in the cell. The cell can be a mammalian cell and it can be present in cell culture (in vitro) or inside a body (in vivo).

The present invention is preferably directed to a method for treating cystic fibrosis, wherein the genetic disorder is preferably the deltaF508 mutation and the sequence to be altered is preferably the (pre-)mRNA of the CFTR harboring the deltaF508 mutation. The present invention is preferably used to repair the RNA of patients with the Cystic Fibrosis Transmembrane conductance Regulator (CFTR) mutation ΔF508. Introduction of 5'-UUU-3' or 5'-CUU-3' in place of the three deleted nucleotides will result in a repaired RNA that restores the missing phenylalanine amino acid (F or Phe) in the protein sequence and therefore result in formation of a wild type protein.

CFTR ΔF508 RNA can for example be repaired by contacting and/or transfecting cells, preferably mammalian cells, more preferably human cells, in vitro or in vivo with an oligonucleotide according to the invention.

A preferred oligonucleotide according to the invention is complementary to a sequence having at least 75%, 80%, 85%, 90%, 95%, 99%, or 100% sequence identity to nucleotides 16-30 and 34-48 of SEQ ID NO: 6 and the altered sequence is preferably selected from 5'-UUU-3' and 5'-CUU-3', preferably 5'-CUU-3'. A more preferred oligonucleotide according to the invention is an oligonucleotide comprising or consisting of SEQ ID NO: 1 or SEQ ID NO: 3, preferably, SEQ ID NO: 1; or an oligonucleotide comprising or consisting of a shortened variant of SEQ ID NO: 1 or SEQ ID NO: 3, preferably SEQ ID NO: 1. Such shortened variant has removed some, e.g. 1, 2, 3, 4, 5, 6, 7, 8, 9, 10, 11, 12 nucleotides from the 3' and/or 5' end of SEQ ID NO: 1 or SEQ ID NO: 3. A preferred variant oligonucleotide according to the invention comprises nucleotides 7 to 29 of SEQ ID NO: 1 or SEQ ID NO: 3, preferably of SEQ ID NO: 1.

```
SEQ ID NO: 1;
5'-AUCAUAGGAAACACCAAAGAUGAUAUUUUCUUU-3' (CAPS nucleotides are preferably 2'-O-Me modified RNA).

SEQ ID NO: 3;
5'-AUCAUAGGAAACACCAAAAAUGAUAUUUUCUUU-3' (CAPS nucleotides are preferably 2'-O-Me modified RNA).
```

A further preferred oligonucleotide according to the invention includes an oligonucleotide comprising or consisting of an oligonucleotide with a sequence selected from the group SEQ ID NO: 16 to SEQ ID NO: 24, or an oligonucleotide comprising or consisting of a shortened variant of an oligonucleotide with a sequence selected from the group of SEQ ID NO: 16 to SEQ ID NO: 24. Such shortened variant has removed some, e.g. 1, 2, 3, 4, 5, 6, 7, 8, 9, 10, 11, 12 nucleotides from the 3' and/or 5' end of SEQ ID NO: 16 to SEQ ID NO: 24. Such oligonucleotides can conveniently be used to make a change in the sequence of a target RNA molecule by e.g. a frameshift insertion of 1 or 2 basepairs at the deleted codon for Phenylalanine (for illustration purposes) an in frame insertion of a nucleoside triplet creating a codon for Phenylalanine in amino acid position 508 of the CFTR protein, an in frame insertion of a nucleoside triplet creating a codon for Leucine in amino acid position 508 or another amino acid position of the CFTR protein, or for inserting a stop codon in the CFTR coding sequence. The mode of action of these exemplary oligonucleotides according to the invention, the molecules depicted in SEQ ID NO: 16 to 24, is depicted in FIGS. 7B-8F.

Preferably, in an oligonucleotide according to the invention, some, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides comprise a modification as described previously herein, or combinations thereof, preferable the nucleotides 2'-O-Me modified. Other stability-enhancing features as described previously herein may be added to the sequences, such as the use of LNA or PNA nucleotides or phosphorothioate bonds between some or all nucleotides. Alternatively DNA nucleotides might be used instead of RNA nucleotides. All or some of the described modifications could be combined in one antisense molecule.

The above described modifications might enhance uptake in epithelial cells. Alternatively, the molecule might be shortened by removal of some, e.g. 1, 2, 3, 4, 5, 6, 7, 8, 9, 10, 11, 12 nucleotides from the 3' and/or 5' end to enhance uptake in cells.

For application in vivo, an oligonucleotide according to the invention may be packaged for delivery (administration) in a liposome, polysome, or nanoparticle or other suitable particle, such as a viral particle. Alternatively, or in combination with the delivery vehicles, the repair molecules might be complexed to polyethylene-imine (PEI) and/or polyethylene glycol (PEG). Oligonucleotides according to the invention may be synthesized inside a cell, even in vivo, for example by infecting cells with a virus or virus-like particle encoding the oligonucleotide. Alternatively, living cells may be transfected—in vitro or in vivo—with (viral) DNA or a plasmid or the like. Upon infection or transfection of the living cell the oligonucleotide according to the invention is synthesized inside the living cell through normal transcription and/or replication, Accordingly, an oligonucleotide according to the invention may be delivered as such, directly to cell, tissue or organ of a multicellular organism. An oligonucleotide according to the invention may also be administrated indirectly using any suitable means known in the art. An oligonucleotide accordingly to the invention may for example be provided to a cell, tissue or organ of a multicellular organism in the form of a vector or an expression vector wherein the vector or expression vector comprises a nucleic acid molecule encoding the oligonucleotide. The expression vector is preferably introduced into a cell, tissue, organ of a multicellular organism via a gene delivery vehicle. In an embodiment, there is provided a viral vector comprising an expression cassette or a transcription cassette that drives expression or transcription of the oligonucleotide according to the invention. A preferred delivery vehicle is a viral vector such as an adeno-associated virus vector (AAV), or a retroviral vector such as a lenti virus vector and the like.

An embodiment of the invention concern the use of a vector comprising a nucleic acid molecule as defined above, wherein the vector is a vector that is suitable for gene therapy. Vectors that are suitable for gene therapy are described in Anderson 1998, Nature 392: 25-30; Walther and Stein, 2000, Drugs 60: 249-71; Kay et al, 2001, Nat. Med. 7: 33-40; Russell, 2000, J. Gen. Virol. 81: 2573-604; Amado and Chen, 1999, Science 285: 674-6; Federico, 1999, Curr. Opin. Biotechnol. 10: 448-53; Vigna and Naldini, 2000, J. Gene Med. 2: 308-16; Marin et al, 1997, Mol. Med. Today 3: 396-403; Peng and Russell, 1999, Curr. Opin. Biotechnol. 10: 454-7; Sommerfelt, 1999, J. Gen. Virol. 80: 3049-64; Reiser, 2000, Gene Ther. 7: 910-3; and references cited therein.

A particularly suitable gene therapy vector includes an Adenoviral and Adeno-associated virus (AAV) vector. These vectors infect a wide number of dividing and non-dividing cell types. In addition adenoviral vectors are capable of high levels of transgene expression. However, because of the episomal nature of the adenoviral and AAV vectors after cell entry, these viral vectors are most suited for therapeutic applications requiring only transient expression of the transgene (Russell, 2000, J. Gen. Virol. 81: 2573-2604; Goncalves, 2005, Virol J. 2(1):43) as indicated above. Preferred adenoviral vectors are modified to reduce the host response as reviewed by Russell (2000, supra).

A preferred retroviral vector for application in the present invention is a lentiviral based expression construct. Lentiviral vectors have the unique ability to infect non-dividing cells (Amado and Chen, 1999 Science 285: 674-6). Methods for the construction and use of lentiviral based expression constructs are described in U.S. Pat. Nos. 6,165,782, 6,207, 455, 6,218,181, 6,277,633 and 6,323,031 and in Federico (1999, Curr Opin Biotechnol 10: 448-53) and Vigna et al. (2000, J Gene Med 2000; 2: 308-16).

Generally, gene therapy vectors will be considered expression vectors described above in the sense that they comprise a nucleic acid molecule encoding an oligonucleotide according to the invention to be expressed, whereby said nucleic acid molecule is operably linked to appropriate regulatory sequences. Such regulatory sequence will at least comprise a promoter sequence. Suitable promoters for expression of a nucleotide sequence encoding a polypeptide from gene therapy vectors include e.g. cytomegalovirus (CMV) intermediate early promoter, viral long terminal repeat promoters (LTRs), such as those from murine moloney leukaemia virus (MMLV) rous sarcoma virus, or HTLV-1, the simian virus 40 (SV 40) early promoter and the herpes simplex virus thymidine kinase promoter.

Many medicines intended for the lung can be applied via the airway. One such a medicine could consist of the RNA repair molecule, i.e. the oligonucleotide according to the invention. A nebulizer is preferably used for delivery of the oligonucleotide according to the invention in an aerosol to the airway epithelial cells. Alternatively a dry powder inhalation formulation could be used. The use of single strand oligonucleotides according to the invention in an airway delivery system reduces the chances of disintegration of the molecule by shearing forces during the administration.

In many diseases the mucus layer shows an increased thickness, leading to a decreased absorption of medicines via the lung. One such a disease is chronical bronchitis, another example is cystic fibrosis. Various forms of mucus normalizers are available, such as DNAses, hypertonic saline or mannitol, which is commercially available under the name of Bronchitol. When mucus normalizers are used in combination with RNA repairing compounds, such as the oligonucleotides according to the invention, they might increase the effectiveness of those medicines. Accordingly, administration of an oligonucleotide according to the invention to a subject, preferably a human subject is preferably combined with mucus normalizers, preferably those mucus normalizers described herein. In addition, administration of the oligonucleotides according to the invention can be combined with administration of small molecule for treatment of CF, such as potentiator compounds for example Kalydeco (ivacaftor; VX-770), or corrector compounds, for example VX-809 (Lumacaftor) and/or VX-661.

Alternatively, or in combination with the mucus normalizers, delivery in mucus penetrating particles or nanoparticles can be applied for efficient delivery of RNA repair molecules to epithelial cells of for example lung and intestine. Accordingly, administration of an oligonucleotide according to the invention to a subject, preferably a human subject, preferably uses delivery in mucus penetrating particles or nanoparticles.

Chronic and acute lung infections are often present in patients with diseases such as cystic fibrosis. Antibiotic treatments reduce bacterial infections and the symptoms of those such as mucus thickening and/or biofilm formation. The use of antibiotics in combination with RNA repair molecules could increase effectiveness of the RNA repair due to easier access of the target cells for the repair molecule. Accordingly, administration of an oligonucleotide according to the invention to a subject, preferably a human subject, is preferably combined with antibiotic treatment to reduce bacterial infections and the symptoms of those such as mucus thickening and/or biofilm formation. The antibiotics can be administered systemically or locally or both.

For application in for example cystic fibrosis patients the oligonucleotides according to the invention, or packaged or complexed oligonucleotides according to the invention may be combined with any mucus normalizer such as a DNase, mannitol, hypertonic saline and/or antibiotics and/or a small molecule for treatment of CF, such as potentiator compounds for example Kalydeco (ivacaftor; VX-770), or corrector compounds, for example VX-809 (Lumacaftor) and/or VX-661.

To increase access to the target cells, Broncheo-Alveolar Lavage (BAL) could be applied to clean the lungs before administration of the oligonucleotides according to the invention.

A time-release capsule can be used for delivery of the oligonucleotides according to the invention to intestinal epithelial cells. CFTR repair in these cells might enhance nutrient uptake. This could be combined with the use of pancreatic enzyme preparations of biological or synthetic origin, such as pancrelipase or Creon which are commercially available and generally used by CF patients to help digestion.

In all embodiments of the present invention, the oligonucleotide according to the invention may be present in a hypertonic saline composition, i.e. a composition comprising an oligonucleotide according to the invention and further comprising 2%-9% saline, preferably 3%-8% saline, more preferably 4%-8% saline, more preferably 5%-8% saline, more preferably 6%-8% saline (such as 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9% or 8.0%), more preferably 6%-7% saline, even more preferably about 7% saline, most preferably 7% saline. Percentage saline herein is defined as weight saline/total volume of the composition, i.e 7% saline corresponds to 70 gram saline/liter composition. The hypertonic saline solution is preferably essentially a NaCl solution.

In any embodiment of the present invention, the oligonucleotide and/or composition according to the invention may be administered according to any way known to the person skilled in the art including but not limited to administration to the lung, preferably via the airways, and systemic administration, preferably intravenous, intramuscular, intradermal or subcutaneous administration.

The person skilled in the art will comprehend that the here above described delivery methods, vehicles and combinations of administration can be further combined in the methods and use according to the present invention, e.g. an oligonucleotide according to the invention and/or a composition comprising such oligonucleotide may be complexed to a delivery compound as described herein, may be packaged in a delivery vehicle described herein and/or may be packaged in a time-release capsule.

One preferred method of delivery is in the form of a viral particle or a viral nucleic acid sequence encoding an oligonucleotide according to the invention, which oligonucleotide is expressed upon infection of a living cell with the viral particle or transfection of the living cell with a viral nucleic acid sequence; preferably as described earlier herein.

Delivery of an oligonucleotide according to the present invention may be to the lung preferably through the airways and/or to the intestine. Administration may be combined with mucus normalizers preferably as described herein and/or with antibiotic treatment preferably as described herein and/or may be combined with the administration of pancreatic enzyme preparations preferably as described herein and/or may be combined with Broncheo-Alveolar Lavage to enhance access to the target cells.

The person skilled in the art will comprehend that two or more oligonucleotides according to the invention may be combined. The person skilled in the art will comprehend that when herein is referred to an oligonucleotide according to the invention, a composition or pharmaceutical composition according to the invention preferably can be interchangeably be used in the methods and uses according to the invention.

In an aspect, the present invention provides for the use of an oligonucleotide for making a change in the sequence of a target RNA molecule present in a living cell, comprising the step of providing the oligonucleotide to the living cell under conditions allowing uptake by the living cell of said oligonucleotide, wherein said oligonucleotide comprises a sequence that is at least partially complementary to the target RNA molecule, such that hybridization of the oligonucleotide to the target RNA, or a precursor thereof, or a template there for, takes place in said living cell, allowing biochemical machinery present in said living cell to copy a difference in sequence of the oligonucleotide relative to the sequence of the target RNA molecule onto the RNA molecule, either directly or via a precursor thereof or a template there for, so as to bring about the change in sequence of said target RNA.

Preferably, in the embodiments of this aspect, the oligonucleotide is an oligonucleotide as described earlier herein.

Preferably, in the embodiments of this aspect, the oligonucleotide is an oligoribonucleotide.

Preferably, in the embodiments of this aspect, the oligonucleotide is provided to the living cell in single stranded form.

Preferably, in the embodiments of this aspect, the living cell is part of a multicellular organism.

Preferably, in the embodiments of this aspect, the living cell is an animal cell, more preferably a human cell.

Preferably, in the embodiments of this aspect, the change in sequence of the target RNA causes the cell to alter its phenotype.

Preferably, in the embodiments of this aspect, the change in said target RNA is confirmed by determining the sequence of said target RNA, or a precursor thereof or template there for.

Preferably, in the embodiments of this aspect, the change in said target RNA is confirmed by determining the sequence of a polypeptide product or of a nucleic acid sequence coding for said polypeptide encoded by said target RNA.

Preferably, in the embodiments of this aspect, the change in said target RNA is confirmed by determining a phenotypic change in said living cell, or the organism comprising said cell.

Preferably, in the embodiments of this aspect, the change is an amelioration of a disorder causally related to the sequence of the target RNA prior to the change.

Preferably, in the embodiments of this aspect, the disorder is a genetic disorder.

Preferably, in the embodiments of this aspect, the oligonucleotide of this aspect has a length of 15-100 nucleotides. More preferably, the length of the oligonucleotide is between 20 and 50, more preferably between 25 and 45 nucleotides, more preferably between 27 and 35 nucleotides.

Preferably, in the embodiments of this aspect, the oligonucleotide comprises an inosine and/or comprises modified nucleotides, preferably selected from the group consisting of a 2'-O alkyl ribose, 2'Fluoro ribose, PMO, 5-methyl-dC, 2-amino-dA, C5-pyrimidine and/or modified internucleoside linkages selected from the group consisting of phosphorothioate linkages, methylphosphonate linkages.

Preferably, in the embodiments of this aspect, the oligonucleotide comprises RNA, DNA, PNA and/or LNA.

Preferably, in the embodiments of this aspect, all nucleosides of the oligonucleotide are 2'-O alkyl ribose nucleosides, more preferably, 2'-O methyl ribose nucleosides.

Preferably, in the embodiments of this aspect, all nucleosides are ribonucleosides.

Preferably, in the embodiments of this aspect, the change in the sequence of the target RNA molecule comprises an insertion or a substitution of one or more nucleosides.

Preferably, in the embodiments of this aspect, the target RNA encodes human CFTR and the change results in the creation or restoration of a nucleoside triplet coding for Phenylalanine in amino acid position 508 of the CFTR protein.

Preferably, in the embodiments of this aspect, the change comprises the insertion of a nucleoside triplet selected from the group consisting of 5'-UUU-3' and 5'-CUU-3'.

Preferably, in the embodiments of this aspect, the oligonucleotide is complementary to a sequence having at least 75%, 80%, 85%, 90%, 95%, or 99% sequence identity to nucleotides 16-30 and 34-48 of SEQ ID NO: 6 and the change comprises the insertion of a nucleoside triplet selected from the group consisting of 5'-UUU-3' and 5'-CUU-3'.

Preferably, in the embodiments of this aspect, the oligonucleotide comprises or consists of nucleotides 7-29, preferably nucleotides 1-33, of SEQ ID NO: 1 or of SEQ ID NO: 3, preferably of SEQ ID NO: 1. Other preferred oligonucleotides include an oligonucleotide comprising or consisting of an oligonucleotide with a sequence selected from the group SEQ ID NO: 16 to SEQ ID NO: 24, or an oligonucleotide comprising or consisting of a shortened variant of an oligonucleotide with a sequence selected from the group of SEQ ID NO: 16 to SEQ ID NO: 24. Such shortened variant has removed some, e.g. 1, 2, 3, 4, 5, 6, 7, 8, 9, 10, 11, 12 nucleotides from the 3' and/or 5' end of SEQ ID NO: 16 to SEQ ID NO: 24.

Preferably, in the embodiments of this aspect, the oligonucleotide is provided in a vehicle, preferably a liposome, polysome, or nanoparticle and/or wherein the oligonucleotide is complexed to a delivery compound, preferably polyethylene-imine (PEI), polyethyleneglycol (PEG), and/or is linked to a sterol, preferably cholesterol.

Preferably, in the embodiments of this aspect, the oligonucleotide is provided to the lung, preferably via the airways, in a dry formulation or in an aerosol preferably using a nebulizer, and preferably the oligonucleotide is provided together with a transfection mediator and/or a cystic fibrosis medicine known to the person skilled in the art, preferably a DNase, mannitol (preferably Bronchitol) and/or a small molecule for treatment of CF, preferably Kalydeco (ivacaftor; VX-770), VX-809 (Lumacaftor) and/or VX-661.

Preferably, in the embodiments of this aspect, the oligonucleotide is provided in a hypertonic saline solution, preferably of between 2%-9% saline concentration, preferably 3%-8%, more preferably 4%-8%, more preferably 5%-8%, more preferably 6%-8%, more preferably 6%-7%, even more preferably about 7% saline concentration, wherein the hypertonic saline solution is preferably a physiologically and pharmaceutically acceptable solution.

Preferably, in the embodiments of this aspect, the hypertonic saline solution is essentially a NaCl solution.

Preferably, in the embodiments of this aspect, the oligonucleotide is administered in a mucus penetrating particle, preferably a mucus penetrating nanoparticle.

Preferably, in the embodiments of this aspect, administration of the oligonucleotide is combined with antibiotic treatment to reduce bacterial infections and the symptoms of those such as mucus thickening and/or biofilm formation.

Preferably, in the embodiments of this aspect, Broncheo-Alveolar Lavage (BAL) is applied before administration of the oligonucleotide according to the invention Preferably, in the embodiments of this aspect, the oligonucleotide is administered in a time-release capsule to facilitate delivery to intestinal cells.

Preferably, in the embodiments of this aspect, the administration of the oligonucleotide is combined with the administration of a biological or synthetic pancreatic enzyme composition such as pancrelipase or Creon.

In a further aspect, the present invention provides for an oligonucleotide for use in the treatment of the human or animal body, wherein said oligonucleotide is capable of making a change in the sequence of a target RNA molecule present in a living cell of said human or animal body, by providing the oligonucleotide to the living cell under conditions allowing uptake by the living cell of said oligonucleotide, wherein said oligonucleotide comprises a sequence that is at least partially complementary to the target RNA molecule, such that hybridization of the oligonucleotide to the target RNA, or a precursor thereof, or a template there for, takes place in said living cell, allowing biochemical machinery present in said living cell to copy a difference in sequence of the oligonucleotide relative to the target RNA molecule onto the RNA molecule, either directly or via a precursor thereof or a template there for, so as to bring about the change in said target RNA.

Preferably, in the embodiments of this aspect, the oligonucleotide is an oligonucleotide as described earlier herein.

Preferably, in the embodiments of this aspect, the oligonucleotide is an oligoribonucleotide.

Preferably, in the embodiments of this aspect, the change in sequence of the target RNA causes the cell to alter its phenotype.

Preferably, in the embodiments of this aspect, the change in the sequence of said target RNA is confirmed by determining the sequence of said target RNA, or a precursor thereof or template there for.

Preferably, in the embodiments of this aspect, the change in the sequence of said target RNA is confirmed by determining the sequence of a polypeptide product encoded by said target RNA.

Preferably, in the embodiments of this aspect, the change in sequence of said target RNA is confirmed by determining a phenotypic change in said living cell, or the organism comprising said cell.

Preferably, in the embodiments of this aspect, the phenotypic change is an amelioration of a disorder causally related to the sequence of the target RNA prior to the change.

Preferably, in the embodiments of this aspect, the disorder is a genetic disorder.

Preferably, in the embodiments of this aspect, the oligonucleotide has a length of 15-100 nucleotides.

Preferably, in the embodiments of this aspect, the length of the oligonucleotide is between 20 and 50, more preferably between 25 and 45 nucleotides, more preferably between 27 and 35 nucleotides.

Preferably, in the embodiments of this aspect, the oligoribonucleotide comprises an inosine and/or comprises modified nucleotides, preferably selected from the group consisting of a 2'-O alkyl ribose, 2'Fluoro ribose, PMO, 5-methyl-dC, 2-amino-dA, C5-pyrimidine and/or modified internucleoside linkages selected from the group consisting of phosphorothioate linkages, methylphosphonate linkages.

Preferably, in the embodiments of this aspect, all nucleosides of the oligonucleotide are 2'-O alkyl ribose nucleosides, more preferably, 2'-O methyl ribose nucleosides.

Preferably, in the embodiments of this aspect, all nucleosides are ribonucleosides.

Preferably, in the embodiments of this aspect, the oligonucleotide comprises RNA, DNA, PNA and/or LNA.

In all embodiments according to the invention, oligonucleotides according to the invention are typically administered in doses ranging from 1 μg to 1000 mg, more preferably from 10 μg to 100 mg, still more preferable from 100 μg to 10 mg, and most preferably from 500 μg to 5 mg, depending on the cell (tissue) to be treated, the weight of the organism, the mode and/or site of administration (local vs. systemic, the site of administration (intraperitoneal, intramuscular, pulmonary, etc.), the disorder to be treated, the regimen to be applied (single or repeated bolus or continuous dosing) and the like. A person having ordinary skill in the art will be capable of establishing the optimal dose using some trial and error.

Preferably, in the embodiments of this aspect, the change in the sequence of the target RNA molecule comprises an insertion or a substitution of one or more nucleosides.

Preferably, in the embodiments of this aspect, the target RNA encodes human CFTR and the change results in the creation or restoration of a nucleoside triplet coding for Phenylalanine in amino acid position 508 of the CFTR protein.

Preferably, in the embodiments of this aspect, the change comprises the insertion of a nucleoside triplet selected from the group consisting of 5'-UUU-3' and 5'-CUU-3'.

Preferably, in the embodiments of this aspect, the oligonucleotide is complementary to a sequence having at least 75%, 80%, 85%, 90%, 95%, or 99% sequence identity to nucleotides 16-30 and 34-48 of SEQ ID NO: 6 and the change comprises the insertion of a nucleoside triplet selected from the group consisting of 5'-UUU-3' and 5'-CUU-3'.

Preferably, in the embodiments of this aspect, the oligonucleotide comprises or consists of nucleotides 7-29, preferably nucleotides 1-33, of SEQ ID NO: 1 or of SEQ ID NO: 3, preferably of SEQ ID NO: 1. Another preferred oligonucleotide includes an oligonucleotide comprising or consisting of an oligonucleotide with a sequence selected from the group SEQ ID NO: 16 to SEQ ID NO: 24, or an oligonucleotide comprising or consisting of a shortened variant of an oligonucleotide with a sequence selected from the group of SEQ ID NO: 16 to SEQ ID NO: 24. Such shortened variant has removed some, e.g. 1, 2, 3, 4, 5, 6, 7, 8, 9, 10, 11, 12 nucleotides from the 3' and/or 5' end of SEQ ID NO: 16 to SEQ ID NO: 24.

Preferably, in the embodiments of this aspect, the oligonucleotide is provided in a vehicle, preferably a liposome, polysome, or nanoparticle and/or wherein the oligonucleotide is complexed to a delivery compound, preferably polyethylene-imine (PEI), polyethyleneglycol (PEG), and/or is linked to a sterol, preferably cholesterol.

Preferably, in the embodiments of this aspect, the oligonucleotide is provided to the respiratory tract or the lung, preferably via the airways, in a dry formulation or in an aerosol preferably using a nebulizer, and preferably the oligonucleotide is provided together with a transfection mediator and/or a cystic fibrosis medicine known to the person skilled in the art, preferably a DNase, mannitol (preferably Bronchitol) and/or a small molecule for treatment of CF, preferably Kalydeco (ivacaftor; VX-770), VX-809 (Lumacaftor) and/or VX-661.

Preferably, in the embodiments of this aspect, the oligonucleotide is provided in a hypertonic saline composition, preferably of between 2%-9% saline concentration, preferably 3%-8%, more preferably 4%-8%, more preferably 5%-8%, more preferably 6%-8%, more preferably 6%-7%, even more preferably about 7% saline concentration, wherein the hypertonic saline solution is preferably a physiologically and pharmaceutically acceptable solution.

Preferably, in the embodiments of this aspect, the hypertonic saline solution is essentially a NaCl solution.

Preferably, in the embodiments of this aspect, the oligonucleotide is provided in a mucus penetrating particle, preferably a mucus penetrating nanoparticle.

Preferably, in the embodiments of this aspect, administration of the oligonucleotide is combined with antibiotic treatment to reduce bacterial infections and the symptoms of those such as mucus thickening and/or biofilm formation.

Preferably, in the embodiments of this aspect, Broncheo-Alveolar Lavage (BAL) is applied before administration of the oligonucleotide according to the invention.

Preferably, in the embodiments of this aspect, the oligonucleotide is administered in a time-release capsule to facilitate delivery to intestinal cells.

Preferably, in the embodiments of this aspect, administration of the oligonucleotide is combined with the administration of a biological or synthetic pancreatic enzyme composition such as pancrelipase or Creon.

In a further aspect, the present invention provides for a pharmaceutical composition comprising an oligonucleotide as defined in the previous aspect of the present invention, a pharmaceutically acceptable carrier and/or a hypertonic physiologically and pharmaceutically acceptable saline solution, preferably of between 2%-9% saline concentration, preferably 3%-8%, more preferably 4%-8%, more preferably 5%-8%, more preferably 6%-8%, more preferably 6%-7%, even more preferably about 7% saline concentration.

Preferably, in the embodiments of this aspect, the hypertonic saline solution is essentially a NaCl solution.

Preferably, in the embodiments of this aspect, the pharmaceutical composition further comprises a transfection mediator.

Preferably, in the embodiments of this aspect, the pharmaceutical composition further comprises a cystic fibrosis medicine known to the person skilled in the art, preferably a DNase, mannitol and/or a small molecule for treatment of CF, preferably Kalydeco (ivacaftor; VXVX-770), VX-809 (Lumacaftor) and/or VX661.

In a further aspect, the present invention provides for an oligonucleotide according to the invention as defined in the various aspects and embodiments herein and/or a pharmaceutical composition comprising such oligonucleotide. Preferably, such oligonucleotide or composition according to the invention is a single stranded oligoribonucleotide or a pharmaceutical composition comprising a single stranded oligoribonucleotide that is complementary to a sequence having at least 75%, 80%, 85%, 90%, 95%, or 99% sequence identity to nucleotides 16-30 and 34-48 of SEQ ID NO: 6. More preferably, such oligonucleotide or composition according to the invention is a single stranded oligoribonucleotide or a pharmaceutical composition comprising a single stranded oligoribonucleotide that comprises nucleotides 7-29, preferably nucleotides 1-33, of SEQ ID NO: 1 or of SEQ ID NO: 3, preferably of SEQ ID NO: 1. Another preferred oligonucleotide includes an oligonucleotide comprising or consisting of an oligonucleotide with a sequence selected from the group SEQ ID NO: 16 to SEQ ID NO: 24, or an oligonucleotide comprising or consisting of a shortened variant of an oligonucleotide with a sequence selected from the group of SEQ ID NO: 16 to SEQ ID NO: 24. Such shortened variant has removed some, e.g. 1, 2, 3, 4, 5, 6, 7, 8, 9, 10, 11, 12 nucleotides from the 3' and/or 5' end of SEQ ID NO: 16 to SEQ ID NO: 24.

In all embodiments of the present invention, an excipient may be used that will (further) aid in enhancing the stability, solubility, absorption, bioavailability, activity, pharmacokinetics, pharmacodynamics and delivery of an oligonucleotide according to the invention to a cell and into a cell, in particular excipients capable of forming complexes, vesicles, nanoparticles, microparticles, nanotubes, nanogels, hydrogels, poloxamers or pluronics, polymersomes, colloids, microbubbles, vesicles, micelles, lipoplexes and/or liposomes, that deliver compound, substances and/or oligonucleotide(s) complexed or trapped in the vesicles or liposomes through a cell membrane. Examples of nanoparticles include gold nanoparticles, magnetic nanoparticles, silica nanoparticles, lipid nanoparticles, sugar particles, protein nanoparticles and peptide nanoparticles. Another group of nanoparticles are polymeric nanoparticles. Many of these polymeric substances are known in the art. Suitable substances comprise e.g. polyethylenimine (PEI), ExGen 500, polypropyleneimine (PPI), poly(2-hydroxypropylenimine (pHP)), dextran derivatives (e.g. polycations such like diethyl amino ethyl amino ethyl (DEAE)-dextran, which are well known as DNA transfection reagent can be combined with butylcyanoacrylate (PBCA) and hexylcyanoacrylate (PHCA) to formulate cationic nanoparticles that can deliver said compound across cell membranes into cells), butylcyanoacrylate (PBCA), hexylcyanoacrylate (PHCA), poly(lactic-co-gly colic acid) (PLGA), polyamines (e.g. spermine, spermidine, putrescine, cadaverine), chitosan, poly(amido amines) (PAMAM), poly(ester amine), polyvinyl ether, polyvinyl pyrrolidone (PVP), polyethylene glycol (PEG) cyclodextrins, hyaluronic acid, colominic acid, and derivatives thereof), dendrimers (e.g. poly(amidoamine), lipids {e.g. 1,2-dioleoyl-3-dimethylammonium propane (DODAP), dioleoyldimethylammonium chloride (DO-DAC), phosphatidylcholine derivatives [e.g 1,2-distearoyl-sn-glycero-3-phosphocholine (DSPC)], lyso-phosphatidyl-choline derivatives [e.g. 1-stearoyl-2-lyso-sn-glycero-3-phosphocholine (S-LysoPC)], sphingomyeline, 2-{3-[bis-(3-amino-propyl)-amino]-propylamino}-N-ditetracedyl carbamoyl methylacetamide (RPR209120), phosphoglycerol derivatives [e.g. 1,2-dipalmitoyl-sn-glycero-3-phosphoglycerol, sodium salt (DPPG-Na), phosphaticid acid derivatives [1,2-distearoyl-sn-glycero-3-phosphaticid acid, sodium salt (DSPA), phosphatidylethanolamine derivatives [e.g. dioleoyl-J-R-phosphatidylethanolamine (DOPE), 1,2-distearoyl-sn-glycero-3-phosphoethanolamine (DSPE), 2-diphytanoyl-sn-glycero-3-phosphoethanolamine (DPhyPE)], JV-[1-(2,3-dioleoyloxy)propyl]-N,N,N-trimethyl ammonium (DOTAP), 1,3-di-oleoyloxy-2-(6-carboxy-spermyl)-propylamid (DOSPER), (1,2-dimyristyolxypropyl-3-dimethylhydroxy ethyl ammonium (DMRIE), (N1-cholesteryloxycarbonyl-3,7-diazanonane-1,9-diamine (CD AN), dimethyldioctadecylammonium bromide (DDAB), 1-palmitoyl-2-oleoyl-sn-glycerol-3-phosphocholine (POPC), (b-L-Arginyl-2,3-L-diaminopropionic acid-N-palmityl-N-olelyl-amide trihydrochloride (AtuFECTOl), N,N-dimethyl-3-aminopropane derivatives [e.g. 1,2-distearoyloxy-N,N-dimethyl-3-aminopropane (DSDMA), 1,2-dioleyloxy-N,N-dimethyl-3-aminopropane (DoDMA), 1,2-dilinoleyloxy-N,N-3-dimethylaminopropane (DLinDMA), 2,2-dilinoleyl-4-dimethylaminomethyl[1,3]-dioxolane (DLin-K-DMA), phosphatidylserine derivatives [1,2-dioleyl-sn-glycero-3-phospho-L-serine, sodium salt (DOPS)], cholesterol}, synthetic amphiphils (SAINT-18), lipofectin, proteins (e.g. albumin, gelatins, atellocollagen), peptides (e.g. PepFects, NickFects, polyarginine, polylysine, CADY, MPG)" combinations thereof and/or viral capsid proteins that are capable of self assembly into particles that can deliver said compound or oligonucleotide to a cell. Lipofectin represents an example of a liposomal transfection agent. It consists of at least two lipid components, a cationic lipid N-[1-(2,3-dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. In addition to these nanoparticle materials, the cationic peptide protamine offers an alternative approach to formulate oligonucleotides as colloids. This colloidal nanoparticle system can form so called proticles, which can be prepared by a simple self-assembly process to package and mediate intracellular release of a compound as defined herein. The skilled person may select and adapt any of the above or other commercially available or not commercially available alternative excipients and delivery systems.

The present invention also provides for a method for the prevention or treatment of a disease related to a (genetic) disorder or related to a (genetic) mutation in a subject, comprising administration of an oligonucleotide according to the invention or a composition according to the invention to a subject, preferably a human subject.

The (genetic) disorder, the (genetic) mutation, the oligonucleotide, composition and administration are preferably as described previously herein.

In the description of the invention, the word "genetic" is put between brackets to indicate that mutations in a target RNA molecule do not necessarily have to be genetically encoded. They could be due to (incorrect) RNA editing, aberrant pre-RNA splicing or processing, or any other (unknown) mechanism.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (e.g. of 10) more or less 0.1% of the value.

The sequence information as provided herein should not be so narrowly construed as to require inclusion of erroneously identified nucleotides. The skilled person is capable of identifying such erroneously identified nucleotides and knows how to correct for such errors. In case of sequence errors, the genomic DNA, mRNA and polynucleotide sequences of the cystic fibrosis transmembrane conductance regulator (CFTR) should prevail.

All patent and literature references cited in the present specification are hereby incorporated by reference in their entirety.

The present invention is further described by the following examples which should not be construed as limiting the scope of the invention.

Unless stated otherwise, the practice of the invention will employ standard conventional methods of molecular biology, microbiology and/or biochemistry. Such techniques are described in Sambrook et al. (1989) Molecular Cloning, A Laboratory Manual (2nd edition), Cold Spring Harbor Laboratory, Cold Spring Harbor Laboratory Press; in Sambrook and Russell (2001) Molecular Cloning: A Laboratory Manual, Third Edition, Cold Spring Harbor Laboratory Press, NY; in Volumes 1 and 2 of Ausubel et al. (1994) Current Protocols in Molecular Biology, Current Protocols, USA; and in Volumes I and II of Brown (1998) Molecular Biology LabFax, Second Edition, Academic Press (UK); Oligonucleotide Synthesis (N. Gait editor); Nucleic Acid Hybridization (Hames and Higgins, eds.).

EXAMPLE 1

In Vivo Assessment of QR-010

The phenotype in Cystic Fibrosis (CF) is caused by the absence of functional CFTR protein resulting in a reduced chloride efflux. CFTR is also a negative regulator of the sodium channel ENaC. The absence of CFTR induces ENaC, resulting in hyperabsorption of sodium, further unbalancing the osmotic balance and worsening the CF phenotype. Repair of CFTR increases chloride transport and has as additional effect that sodium hyperabsorption is diminished.

The effectiveness of an agent to treat CFTR can be measured by determining nasal potential difference (NPD) in a cystic fibrosis mouse model (Leal et al, 2006, Lab animals 40: 43-52). NPD measurements are a way to measure currents over the nasal epithelium in animals and humans. Herein, in the trace that is generated during the measurement sodium transport is determined by calculating the difference between the current at the start and after addition of an ENaC blocker. For the CFTR activity the difference between pre and post chloride-minus buffer and/or forskolin application is determined.

Decrease of the potential indicates an effective treatment due to decrease of the ENaC hyperactivity observed in CF. Sodium is transported by ENaC, which is regulated by CFTR. Because of the absence of functional CFTR in CF ENaC is not downregulated resulting in hyper absorption of sodium, which in its turn worsens the CF phenotype.

Increase of the potential by forskolin induction also indicates effective treatment. Typically, in CF mice there is no chloride-minus CFTR response and no forskolin induced CFTR response; if a statistically significant correction of the forskolin induced CFTR response can be observed after treatment, this is an indication of effective treatment.

In brief, eight CF-dF508 mice were treated with ProQR's QR-010 molecule (an oligonucleotide with the sequence as depicted in SEQ ID NO: 1). The mice had multiple intranasal administrations of 40 µg QR-010 solved in 2 µL water. The mice had a pre-treatment NPD measurement at day 0, administration of the molecule at day 2, 4 and 7 and post-treatment NPD measurement at day 9. Three mice were subsequently dosed at day 10, 13 and 15 and post-treatment measurement at day 17, NPD measurement was performed as follows according to Leal et al, 2006, Lab animals 40: 43-52, with some modifications, and using a data memory high-impedance (>1.0 E+12Ω) voltmeter (Knick Portamesss 913, Elektronische Meßgeräte, Berlin, Germany). Briefly, mice were placed on their backs on a heating pad, and paws and tail were taped out of the way. An intravenous catheter with wings (0.719 mm, Insyte-Wt, Becton Dickinson, Utah, USA), filled with a diluted electrode cream (Signa [Parker Labs, Fairfield, N.J., USA] cream/KCl 1 mol/L 1:1 vol/vol) and inserted subcutaneously in a hind leg, served as a bridge for connecting the reference Ag/AgCl electrode (SLE Instruments, South Croydon, UK). A double-lumen catheter (outer diameter [OD] r0.3 mm) was placed in a nasal passage, one lumen being used for perfusion of isotonic saline-buffered solutions, and the other serving as measuring electrode. Its impedance was <1.0 E+6Ω. The tongue of the animal was displaced sideways and a pointed wick of filter paper was inserted in the mouth for about 1 cm towards the throat in order to absorb excess liquid from the oral cavity. Excess fluid running out of the perfused nostril was absorbed by a filter paper held at the tip of the nose, in such a way that the opposite nostril remained free of solution. Usually, 5 min after injection of drugs, the heating pad was gently tilted by about 30 degrees, with the animal head downwards, and nasal perfusion began at a rate of 15 mL/min using a peristaltic pump (P1, Amersham Biosciences, Roosendaal, The Netherlands). Before starting the perfusion, the baseline nasal PD was measured until a stable value was obtained. Solutions were changed only after the voltage had stabilized. The basal isotonic saline solution consisted of (mmol/L): $Na^+$ 140, $Cl^-$ 120, $K^+$ 5.2, $HCO_3^-$ 25, $HPO_4^{2-}$ 2.4, $H_2PO_4^-$ 0.4, $Ca^{2+}$ 1.2, and $Mg^{2+}$ 1.2. The chloride-free solution used to detect chloride efflux from the nasal epithelium was prepared by substituting NaCl and $CaCl_2$ with equimolar gluconate, and $MgCl_2$ with $MgSO_4$. Osmolarity was 275 mOsm/L and pH was 7.4. The starting NPD value is mainly due to the sodium current generated by ENaC. This channel was blocked with amiloride to reduce the potential to zero. Chloride-free buffer is added to measure the chloride transported by CFTR and forskoline is used to activate CFTR. At the end of the experiment, a fixed dose of naloxone (4 mg), a competitive morphinic antagonist, and atipamezole, a medetomidine-specific antidote (5 times the dose of medetomidine), were administered and the animal was kept in a dark room on a heating pad until full recovery, which usually occurred 3-4 h afterwards.

Figure 5:
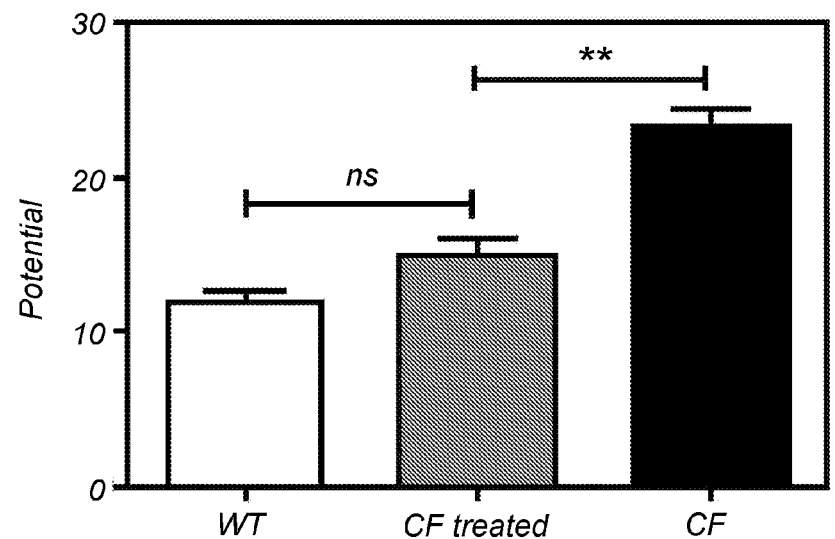
Figure 6:
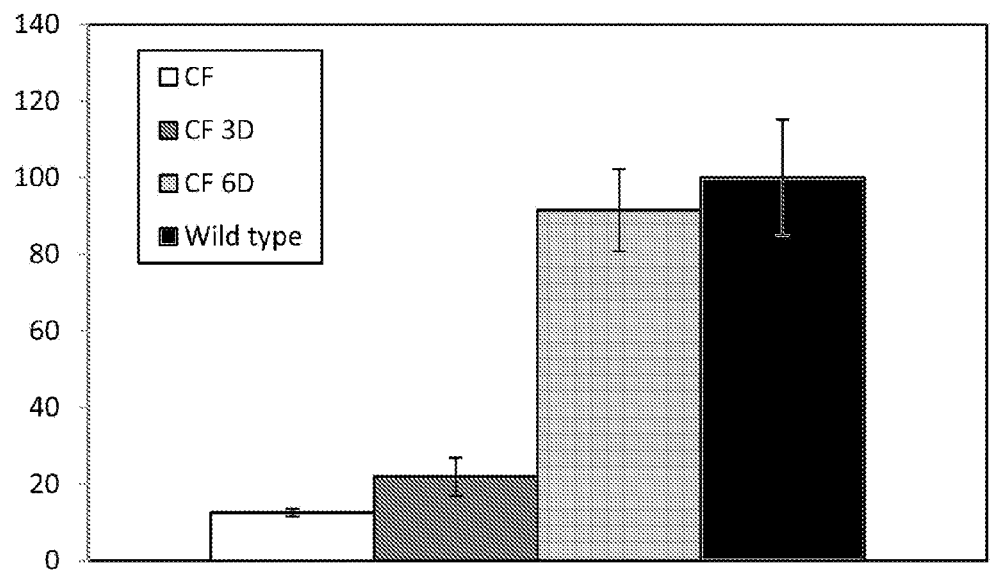

The results of the NPD measurements are depicted in FIGS. 5 and 6.

In FIG. 5, it is clearly depicted that sodium transport in CF mice is altered upon treatment with QR-010 (p=0.0002; n=8), moving towards wild-type levels. This is a concrete indication that CFTR activity is restored upon treatment with QR-010.

In FIG. 6, it is clearly depicted that the forskolin-induced CFTR response is improved after 3 doses of QR-010 (p=0.019; n=8), with a further improvement after 6 doses of QR-010 (p=0.11, n=3) Typically, in CF mice there is no forskolin induced CFTR response; however after treatment a correction of the forskolin induced CFTR response is observed. This is a concrete indication that CFTR activity is restored upon treatment with QR-010.

Altogether, the present experiment clearly demonstrates that an oligonucleotide according to the invention such as QR-010 is effective in repairing gene defects.

EXAMPLE 2

Activity in Restoring the RNA Sequence Coding for Wild-Type CFTR of the Oligonucleotides Depicted in SEQ ID NO's: 51, 56, 61 and 66

The oligonucleotides depicted in SEQ ID NO's: 51, 56, 61 and 66, are tested for their activity in restoring the RNA sequence coding for wild-type CFTR in primary lung epithelial cells obtained from patients carrying the targeted mutation on at least one allele. The cells are cultured according to methods known to the person skilled in the art in an appropriate medium. The oligonucleotides according to the invention are introduced into the cells by transfection. Transfection is performed according to methods known to the person skilled in the art with the aid of the transfection reagent lipofectamine, at concentrations ranging from 1 to 500 nM. The oligo-transfection reagent complex is added to the cells in the appropriate medium and washed from the cells after 24 h incubation.

The activity in restoring the RNA sequence coding for wild-type CFTR of the oligonucleotides is determined after 1 to 4 days of cell culture after transfection. Cells are harvested and the activity of the oligonucleotides is assessed on a molecular level using RNA repair as the primary read-out. RNA repair is determined by sequencing and/or Q-PCR methods. RNA is purified from the cells using a method known to the person skilled in the art. Subsequently, the part of the CFTR RNA wherein the targeted mutation is present is amplified by RT-PCR. The RT-PCR products are sequenced to determine that the mutation has been repaired as depicted in FIGS. 9A-D.

FIGURE LEGENDS

FIG. 1. Partial sequences of wild type (WT) and ΔF508 (Mut) CFTR RNA surrounding the deletion site. The three nucleotides deleted in the mutant are depicted in boldface in the WT sequence.

FIG. 2. Schematic representation of RNA editing of the mutant ΔF508 CFTR RNA using an oligonucleotide with SEQ ID NO: 1. The repaired RNA molecule (RS) has 3 nucleotides inserted, rendering the RNA sequence identical to wild-type CFTR.

FIG. 3. Partial RNA and protein sequences of the wild type, mutant and repaired molecules. The mutant misses the phenylalanine at position 508. The repaired RNA results in insertion of a phenylalanine, resulting a wild type protein sequence.

FIG. 4. Activity of the single strand oligonucleotide in endogenous ΔF508 mutant CFTR expressing cell cultures. Single strand oligonucleotide and previously described duplex oligonucleotide are compared. Activity is measured by detection of CFTR chloride transporter activity.

FIG. 5. ENaC activity depicted as potential (mV) for wild-type mice (WT), CF mice (CF) and CF mice treated with QR-010 (CF-treated). **P<0.01; ns=not significant. Bars show standard error of the mean (SEM); p-values were obtained by unpaired T-test.

FIG. 6. Forskolin-induced CFTR response depicted as relative percentage for wild-type mice (Wild type), untreated CF mice (CF), CF mice treated with 3 doses QR-010 (CF 3D) and CF mice treated with 6 doses QR-010 (CF 6D). Wild-type mice are depicted as 100%.

FIG. 7A. Repair of the CFTR delta F508 mutation in a target RNA by the 010 g oligonucleotide (SEQ ID NO: 1) is depicted; part of the RNA surrounding the deletion site is shown. The inserted trinucleoside CUU resulting in the appearance of a Phenylalanine (F) at position 508 (UUU) is emphasized in bold.

FIG. 7B. Insertion of two nucleosides at position 508 in the delta F508 CFTR target RNA by an oligonucleotide with the sequence of SEQ ID NO: 16 is depicted; part of the RNA surrounding the deletion site is shown. The insertion of two nucleosides CU at position 508 is depicted, causing a frameshift in the coding sequence.

FIG. 7C. Insertion of one nucleoside at position 508 in the delta F508 CFTR target RNA by an oligonucleotide with the sequence of SEQ ID NO: 17 is depicted; part of the RNA surrounding the deletion site is shown. The insertion of the nucleoside C at position 508 is depicted, causing a frameshift in the coding sequence, ultimately creating a stopcodon at position 512.

FIG. 7D. The insertion of one nucleoside at position 508 in the delta F508 CFTR target RNA by an oligonucleotide with the sequence of SEQ ID NO: 18 is depicted; part of the RNA surrounding the deletion site is shown. The insertion of the nucleoside C at position 508 is depicted, causing a frameshift in the coding sequence, ultimately creating a stopcodon at position 512.

FIG. 8. Various insertions at position 508 in the WT CFTR target RNA are depicted.

FIG. 8A. Insertion of a stopcodon at position 508 (ATCATCTGATTTGGTGTT); SEQ ID NO: 33) in the WT CFTR target RNA by an oligonucleotide with the sequence of SEQ ID NO: 19 is depicted; part of the RNA surrounding the 508 position is shown. The insertion of the stopcodon causes a translation stop after I 507.

FIG. 8B. The insertion of two nucleosides at position 508 in the WT CFTR target RNA by an oligonucleotide with the sequence of SEQ ID NO: 20 is depicted; part of the RNA surrounding the 508 position is shown. The insertion of two nucleosides GA at position 508 is depicted, causing a frameshift in the coding sequence.

FIG. 8C. The insertion of one nucleoside at position 508 in the WT CFTR target RNA by an oligonucleotide with the sequence of SEQ ID NO: 21 is depicted; part of the RNA surrounding the 508 position is shown. The insertion of nucleoside A at position 508 is depicted, causing a frameshift in the coding sequence, ultimately creating a stopcodon at position 513.

FIG. 8D. The insertion of a leucine codon (ATCATCCTCTTTGGTGTT; SEQ ID NO: 40) at position 508 in the WT CFTR target RNA by an oligonucleotide with the sequence of SEQ ID NO: 22 is depicted; part of the RNA surrounding the 508 position is shown. The insertion of the leucine codon and resulting polypeptide is shown.

FIG. 8E. Insertion of a stopcodon halfway in exon 10 of the WT CFTR target RNA by an oligonucleotide with the sequence of SEQ ID NO: 23 is depicted; part of the RNA surrounding the 508 position is shown. The insertion of the stopcodon causes a translation stop after amino acid position F 494.

FIG. 8F. The introduction of a leucine codon (CUU) in exon 10 of the WT CFTR target RNA by an oligonucleotide with the sequence of SEQ ID NO: 24 is depicted. The introduction of the leucine codon and resulting polypeptide is shown.

Figure 9A:
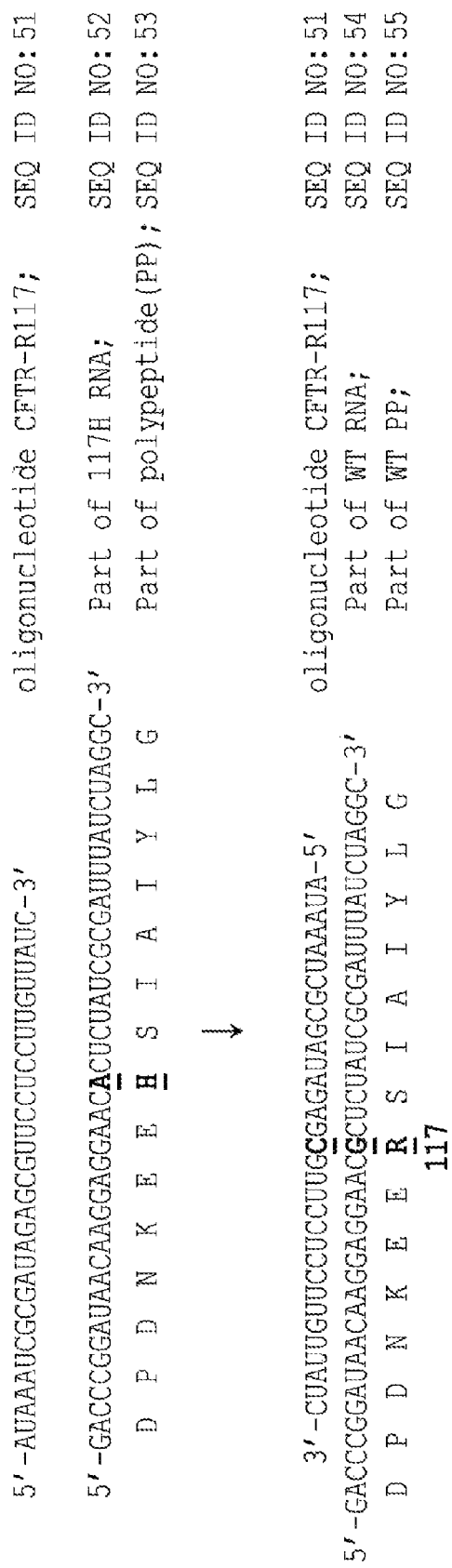

FIG. 9A. Repair of the CFTR R117H mutation in a target RNA by the CFTR-R117 oligonucleotide (SEQ ID NO: 51) is depicted; part of the RNA surrounding the mutation site is shown. The substitution of "A" for "G" transforms the CAC codon (His) into a CGC codon (Arg) and is emphasized in bold.

Figure 9B:
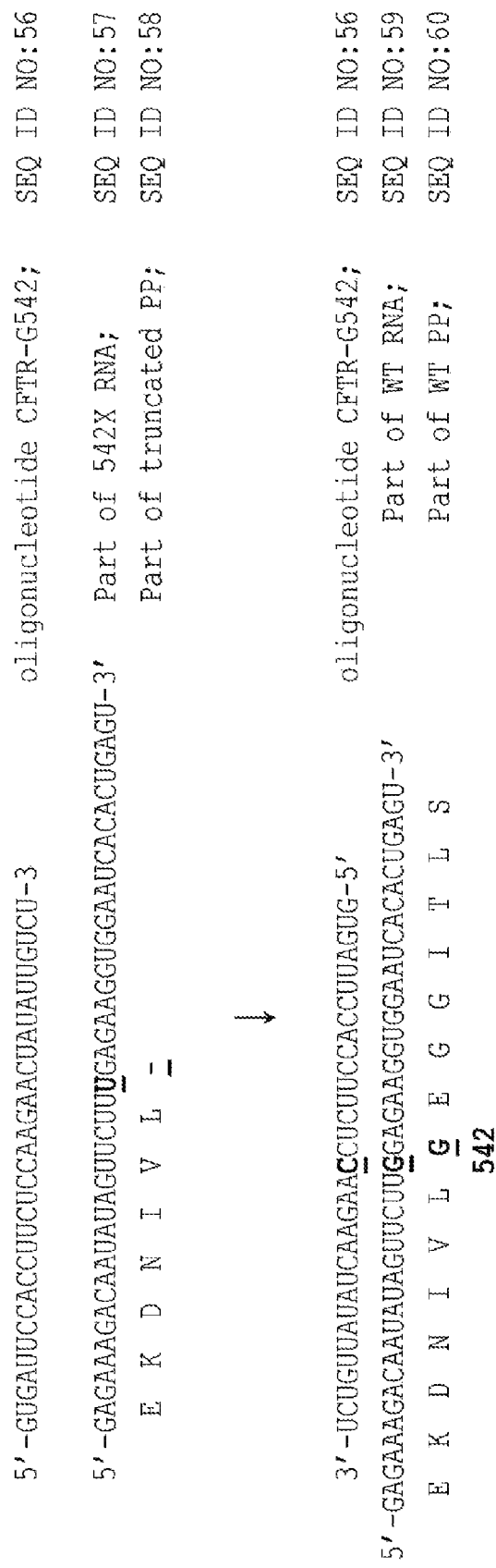

FIG. 9B. Repair of the CFTR G542X mutation in a target RNA by the CFTR-G542 oligonucleotide (SEQ ID NO: 56) is depicted; part of the RNA surrounding the mutation site is shown. The substitution of "U" for "G" transforms the UGA codon (Stop) into a GGA codon (Gly) and is emphasized in bold.

Figure 9C:
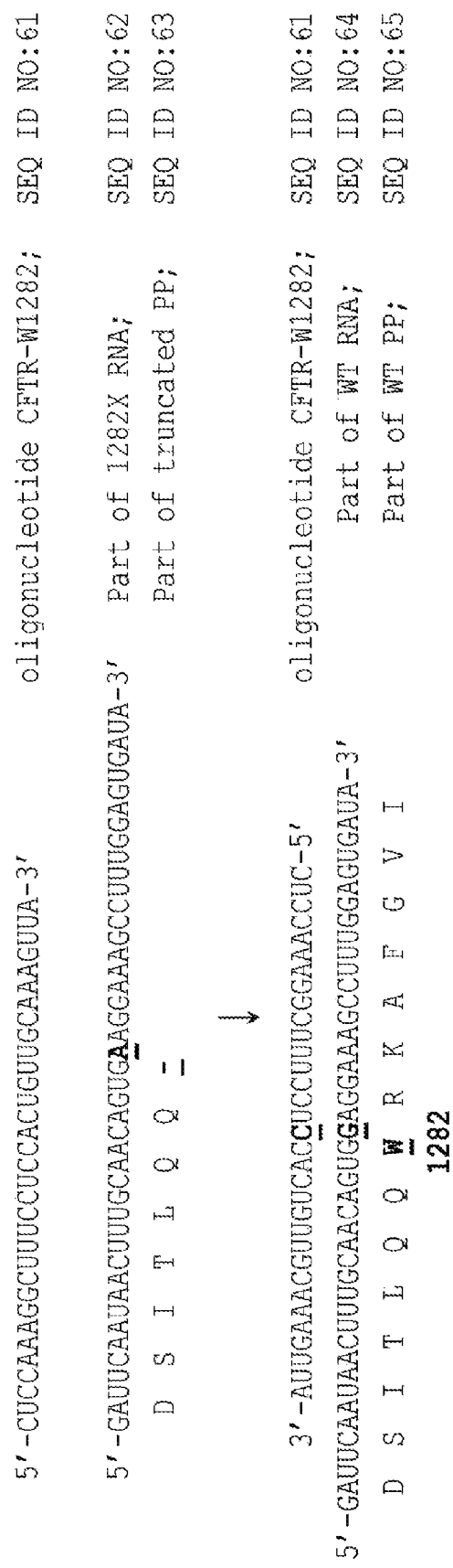

FIG. 9C. Repair of the CFTR W1282X mutation in a target RNA by the CFTR-W1282 oligonucleotide (SEQ ID NO: 61) is depicted; part of the RNA surrounding the mutation site is shown. The substitution of "A" for "G" transforms the UGA codon (Stop) into a UGG codon (Tryp) and is emphasized in bold.

FIG. 9D. Repair of the CFTR N1303K mutation in a target RNA by the CFTR-N1303 oligonucleotide (SEQ ID NO: 66) is depicted; part of the RNA surrounding the mutation site is shown. The substitution of "G" for "C" transforms the AAG codon (Lys) into a AAC codon (Asn) and is emphasized in bold.

The invention claimed is:

1. A method of making a change in the sequence of a target RNA molecule in a living cell of a human or animal subject, the method comprising providing a single-stranded non-duplexed oligonucleotide capable of making a change in the sequence of the target RNA molecule to a living cell of the subject under conditions that permit uptake of the oligonucleotide by the cell, wherein all nucleosides of the oligonucleotide are 2'-O alkyl ribose ribonucleosides and the oligonucleotide comprises a sequence that is at least partially complementary to the target RNA molecule, to make the change in the target RNA, wherein the change in the sequence of the target RNA comprises an insertion or a substitution of one or more nucleosides, and wherein the target RNA encodes human CFTR protein, and the change in the sequence of the target RNA results in the creation or restoration of a nucleoside triplet coding for phenylalanine at amino acid position 508 of the CFTR protein.

2. The method of claim 1, wherein the change in the sequence of the target RNA is confirmed by determining the sequence of the target RNA, or a precursor thereof, or by determining the sequence of a polypeptide product encoded by the target RNA.

3. The method of claim 1, wherein the oligonucleotide has a length between 15 and 100 nucleotides, between 20 and 50 nucleotides, between 25 and 45 nucleotides, or between 27 and 35 nucleotides.

4. The method of claim 1, wherein the oligonucleotide comprises an internucleoside linkage selected from the group consisting of phosphorothioate linkage and methylphosphonate linkage.

5. The method of claim 1, wherein the change in the sequence of the target RNA comprises the insertion of a nucleoside triplet selected from the group consisting of 5'-UUU-3' and 5'-CUU-3'.

6. The method of claim 5, wherein the oligonucleotide is complementary to a sequence having at least 75%, 80%, 85%, 90%, 95%, or 99% sequence identity to nucleotides 16-30 and 34-48 of SEQ ID NO: 6.

7. The method of claim 1, wherein the oligonucleotide is provided in a vehicle selected from the group consisting of a liposome, a polysome, and a nanoparticle.

8. The method of claim 1, wherein the oligonucleotide is complexed to a delivery compound selected from the group consisting of polyethylene-imine (PEI) and polyethyleneglycol (PEG).

9. The method of claim 1, wherein the oligonucleotide is linked to a sterol.

10. The method of claim 9, wherein the sterol is cholesterol.

11. The method of claim 1, wherein the oligonucleotide is provided to the respiratory tract or the lung of the subject.

12. The method of claim 11, wherein the oligonucleotide is provided in a dry formulation or in an aerosol.

13. The method of claim 11, wherein the oligonucleotide is provided using a nebulizer.

14. The method of claim 11, wherein the oligonucleotide is provided together with a transfection mediator.

15. The method of claim 11, wherein the oligonucleotide is provided together with a drug for treating cystic fibrosis.

16. The method of claim 15, wherein the drug is selected from the group consisting of a DNase, mannitol, ivacaftor, and lumacaftor.

17. The method of claim 11, wherein the oligonucleotide is provided in a composition comprising a hypertonic saline solution.

18. The method of claim 17, wherein the concentration of the saline is about 7%.

19. The method of claim 11, wherein the oligonucleotide is provided in a mucus penetrating particle.

20. The method of claim 19, wherein the particle is a nanoparticle.

21. The method of claim 11, wherein administration of the oligonucleotide is combined with antibiotic treatment to reduce bacterial infections and the symptoms of such infections including mucus thickening and/or biofilm formation.

22. The method of claim 11, wherein Broncheo-Alveolar Lavage (BAL) is applied before administration of the oligonucleotide.

23. The method of claim 1, wherein the oligonucleotide is administered in a time-release capsule to facilitate delivery to intestinal cells of the subject.

24. The method of claim 23, wherein the oligonucleotide is administered in combination with a biological or synthetic pancreatic enzyme composition.

25. The method of claim 1, wherein the oligonucleotide is provided in a pharmaceutical composition comprising a pharmaceutically acceptable carrier.

26. The method of claim 25, wherein the pharmaceutical composition comprises a hypertonic, pharmaceutically acceptable saline solution.

27. The method of claim 1, wherein all nucleosides of the oligonucleotide are 2'-O methyl ribose ribonucleosides.

28. A method of making a change in the sequence of a target RNA molecule in a living cell of a human or animal subject, the method comprising providing a single-stranded non-duplexed oligonucleotide to a living cell of the subject under conditions that permit uptake of the oligonucleotide by the cell, wherein all nucleosides of the oligonucleotide are 2'-O alkyl ribose ribonucleosides and the oligonucleotide comprises a sequence that is at least partially complementary to the target RNA molecule and the oligonucleotide comprises nucleotides 7-29 of SEQ ID NO: 1.

29. The method of claim 28, wherein the oligonucleotide comprises the nucleotide sequence of SEQ ID NO: 1.

30. The method of claim 28, wherein all nucleosides of the oligonucleotide are 2'-O methyl ribose ribonucleosides.

31. A method of making a change in the sequence of a target RNA molecule in a living cell of a human or animal subject, the method comprising providing a single-stranded non-duplexed oligonucleotide to a living cell of the subject under conditions that permit uptake of the oligonucleotide by the cell, wherein all nucleosides of the oligonucleotide are 2'-O alkyl ribose ribonucleosides and the oligonucleotide comprises a sequence that is at least partially complementary to the target RNA molecule and the oligonucleotide comprises nucleotides 7-29 of SEQ ID NO: 3.

32. The method of claim 31, wherein the oligonucleotide comprises the nucleotide sequence of SEQ ID NO: 3.

* * * * *

SEQUENCE LISTING

```
<160> NUMBER OF SEQ ID NOS: 70

<210> SEQ ID NO 1
<211> LENGTH: 33
<212> TYPE: RNA
<213> ORGANISM: Artificial
<220> FEATURE:
<223> OTHER INFORMATION: Oligonucleotide

<400> SEQUENCE: 1
aucauaggaa acaccaaaga ugauauuuuc uuu                                      33

<210> SEQ ID NO 2
<211> LENGTH: 11
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: U is phosphorylated
<220> FEATURE:
<221> NAME/KEY: misc_feature
<222> LOCATION: (11)..(11)
<223> OTHER INFORMATION: U is phosphorylated

<400> SEQUENCE: 2
ucauuuuugg u                                                              11
```

```
<210> SEQ ID NO 3
<211> LENGTH: 33
<212> TYPE: RNA
<213> ORGANISM: Artificial
<220> FEATURE:
<223> OTHER INFORMATION: Oligonucleotide

<400> SEQUENCE: 3
aucauaggaa acaccaaaaa ugauauuuuc uuu                                    33

<210> SEQ ID NO 4
<211> LENGTH: 11
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: U is phosphorylated
<220> FEATURE:
<221> NAME/KEY: misc_feature
<222> LOCATION: (11)..(11)
<223> OTHER INFORMATION: U is phosphorylated

<400> SEQUENCE: 4
ucaucuuugg u                                                            11

<210> SEQ ID NO 5
<211> LENGTH: 63
<212> TYPE: RNA
<213> ORGANISM: Artificial
<220> FEATURE:
<223> OTHER INFORMATION: Part of exon 10  of the CFTR transcript

<400> SEQUENCE: 5
uaugccuggc accauuaaag aaaauaucau cuuuggucuu uccuaugaug aauauagaua       60
cag                                                                    63

<210> SEQ ID NO 6
<211> LENGTH: 60
<212> TYPE: RNA
<213> ORGANISM: Artificial
<220> FEATURE:
<223> OTHER INFORMATION: Part of exon 10 of the CFTR transcript

<400> SEQUENCE: 6
uaugccuggc accauuaaag aaaauaucau ugguguuucc uaugaugaau auagauacag       60

<210> SEQ ID NO 7
<211> LENGTH: 30
<212> TYPE: RNA
<213> ORGANISM: Artificial
<220> FEATURE:
<223> OTHER INFORMATION: Part of exon 10 of the CFTR transcript

<400> SEQUENCE: 7
uaugccuggc accauuaaag aaaauaucau                                       30

<210> SEQ ID NO 8
<211> LENGTH: 30
<212> TYPE: RNA
<213> ORGANISM: Artificial
<220> FEATURE:
<223> OTHER INFORMATION: Part of exon 10 of the CFTR transcript

<400> SEQUENCE: 8
```

```
ugguguuucc uaugaugaau auagauacag                                      30
```

<210> SEQ ID NO 9
<211> LENGTH: 63
<212> TYPE: RNA
<213> ORGANISM: Artificial
<220> FEATURE:
<223> OTHER INFORMATION: Part of exon 10 of the CFTR trancript

<400> SEQUENCE: 9

```
uaugccuggc accauuaaag aaauaucau cuuuggguguu uccuaugaug aauauagaua     60
cag                                                                  63
```

<210> SEQ ID NO 10
<211> LENGTH: 60
<212> TYPE: RNA
<213> ORGANISM: Artificial
<220> FEATURE:
<223> OTHER INFORMATION: Part of exon 10 of the CFTR transcript

<400> SEQUENCE: 10

```
augccuggca ccauuaaaga aaauaucauc uuugguguuu ccuaugauga auauagauac     60
```

<210> SEQ ID NO 11
<211> LENGTH: 20
<212> TYPE: PRT
<213> ORGANISM: Artificial
<220> FEATURE:
<223> OTHER INFORMATION: Peptide

<400> SEQUENCE: 11

```
Met Pro Gly Thr Ile Lys Glu Asn Ile Ile Phe Gly Val Ser Tyr Asp
1               5                   10                  15

Glu Tyr Arg Tyr
            20
```

<210> SEQ ID NO 12
<211> LENGTH: 57
<212> TYPE: RNA
<213> ORGANISM: Artificial
<220> FEATURE:
<223> OTHER INFORMATION: Part of exon 10 of the CFTR transcript

<400> SEQUENCE: 12

```
augccuggca ccauuaaaga aaauaucauu ggguguuccu augaugaaua uagauac        57
```

<210> SEQ ID NO 13
<211> LENGTH: 19
<212> TYPE: PRT
<213> ORGANISM: Artificial
<220> FEATURE:
<223> OTHER INFORMATION: Peptide

<400> SEQUENCE: 13

```
Met Pro Gly Thr Ile Lys Glu Asn Ile Ile Gly Val Ser Tyr Asp Glu
1               5                   10                  15

Tyr Arg Tyr
```

<210> SEQ ID NO 14
<211> LENGTH: 60
<212> TYPE: RNA
<213> ORGANISM: Artificial
<220> FEATURE:
<223> OTHER INFORMATION: Part of exon 10 of the CFTR transcript

```
<400> SEQUENCE: 14
augccuggca ccauuaaaga aaauaucauc uuugguguuu ccaugauga auauagauac    60

<210> SEQ ID NO 15
<211> LENGTH: 20
<212> TYPE: PRT
<213> ORGANISM: Artificial
<220> FEATURE:
<223> OTHER INFORMATION: Peptide

<400> SEQUENCE: 15

Met Pro Gly Thr Ile Lys Glu Asn Ile Ile Phe Gly Val Ser Tyr Asp
1               5                   10                  15

Glu Tyr Arg Tyr
            20

<210> SEQ ID NO 16
<211> LENGTH: 32
<212> TYPE: RNA
<213> ORGANISM: Artificial
<220> FEATURE:
<223> OTHER INFORMATION: Oligonucleotide dF-ins1

<400> SEQUENCE: 16
aucauaggaa acaccaagau gauauuuucu uu                                 32

<210> SEQ ID NO 17
<211> LENGTH: 31
<212> TYPE: RNA
<213> ORGANISM: Artificial
<220> FEATURE:
<223> OTHER INFORMATION: Oligonucleotide dF-ins1

<400> SEQUENCE: 17
aucauaggaa acaccagaug auauuuucuu u                                  31

<210> SEQ ID NO 18
<211> LENGTH: 33
<212> TYPE: RNA
<213> ORGANISM: Artificial
<220> FEATURE:
<223> OTHER INFORMATION: Oligonucleotide dF-ins1 33b

<400> SEQUENCE: 18
caucauagga aacaccagau gauauuuucu uua                                33

<210> SEQ ID NO 19
<211> LENGTH: 33
<212> TYPE: RNA
<213> ORGANISM: Artificial
<220> FEATURE:
<223> OTHER INFORMATION: Oligonucleotide CFTR WT X

<400> SEQUENCE: 19
auaggaaaca ccaaaucaga ugauauuuuc uuu                                33

<210> SEQ ID NO 20
<211> LENGTH: 32
<212> TYPE: RNA
<213> ORGANISM: Artificial
<220> FEATURE:
<223> OTHER INFORMATION: Oligonucleotide CFTR WT Ins2

<400> SEQUENCE: 20
auaggaaaca ccaaaucgau gauauuuucu uu                                 32
```

<210> SEQ ID NO 21
<211> LENGTH: 31
<212> TYPE: RNA
<213> ORGANISM: Artificial
<220> FEATURE:
<223> OTHER INFORMATION: Oligonucleotide CFTR WT Ins1

<400> SEQUENCE: 21
auaggaaaca ccaaaugaug auauuuucuu u                                  31

<210> SEQ ID NO 22
<211> LENGTH: 33
<212> TYPE: RNA
<213> ORGANISM: Artificial
<220> FEATURE:
<223> OTHER INFORMATION: Oligonucleotide CFTR WT L

<400> SEQUENCE: 22
auaggaaaca ccaaagagga ugauauuuuc uuu                                33

<210> SEQ ID NO 23
<211> LENGTH: 33
<212> TYPE: RNA
<213> ORGANISM: Artificial
<220> FEATURE:
<223> OTHER INFORMATION: Oligonucleotide CFTR WT OX

<400> SEQUENCE: 23
aggcauaauc caggaucaaa acugagaaca gaa                                33

<210> SEQ ID NO 24
<211> LENGTH: 33
<212> TYPE: RNA
<213> ORGANISM: Artificial
<220> FEATURE:
<223> OTHER INFORMATION: Oligonucleotide CFTR WT OL

<400> SEQUENCE: 24
auggugccag gcauaaggau ccaggaaaac uga                                33

<210> SEQ ID NO 25
<211> LENGTH: 42
<212> TYPE: RNA
<213> ORGANISM: Artificial
<220> FEATURE:
<223> OTHER INFORMATION: Part of deltaF508 RNA

<400> SEQUENCE: 25
accauuaaag aaaauaucau ugguguuucc uaugaugaau au                      42

<210> SEQ ID NO 26
<211> LENGTH: 14
<212> TYPE: PRT
<213> ORGANISM: Artificial
<220> FEATURE:
<223> OTHER INFORMATION: Part of delta F508 polypeptide

<400> SEQUENCE: 26

Thr Ile Lys Glu Asn Ile Ile Gly Val Ser Tyr Asp Glu Tyr
 1               5                  10

<210> SEQ ID NO 27
<211> LENGTH: 45
<212> TYPE: RNA
<213> ORGANISM: Artificial

```
<220> FEATURE:
<223> OTHER INFORMATION: Part of WT RNA

<400> SEQUENCE: 27
accauuaaag aaaauaucau cuuggguguu uccuaugaug aauau            45

<210> SEQ ID NO 28
<211> LENGTH: 15
<212> TYPE: PRT
<213> ORGANISM: Artificial
<220> FEATURE:
<223> OTHER INFORMATION: Part of WT polypeptide

<400> SEQUENCE: 28

Thr Ile Lys Glu Asn Ile Ile Phe Gly Val Ser Tyr Asp Glu Tyr
1               5                   10                  15

<210> SEQ ID NO 29
<211> LENGTH: 45
<212> TYPE: RNA
<213> ORGANISM: Artificial
<220> FEATURE:
<223> OTHER INFORMATION: Part of delta F508 RNA with CU insertion

<400> SEQUENCE: 29
accauuaaag aaaauaucau cugguguuu ccuaugauga auaua             45

<210> SEQ ID NO 30
<211> LENGTH: 15
<212> TYPE: PRT
<213> ORGANISM: Artificial
<220> FEATURE:
<223> OTHER INFORMATION: Part of delta 508 polypeptide, with frameshift

<400> SEQUENCE: 30

Thr Ile Lys Glu Asn Ile Ile Leu Val Phe Pro Met Met Asn Ile
1               5                   10                  15

<210> SEQ ID NO 31
<211> LENGTH: 43
<212> TYPE: RNA
<213> ORGANISM: Artificial
<220> FEATURE:
<223> OTHER INFORMATION: Part of delta F508 RNA, with C insertion

<400> SEQUENCE: 31
accauuaaag aaaauaucau cugguguuuc cuaugaugaa uau              43

<210> SEQ ID NO 32
<211> LENGTH: 11
<212> TYPE: PRT
<213> ORGANISM: Artificial
<220> FEATURE:
<223> OTHER INFORMATION: Part of delta F508 polypeptide with premature
      stop

<400> SEQUENCE: 32

Thr Ile Lys Glu Asn Ile Ile Trp Cys Phe Leu
1               5                   10

<210> SEQ ID NO 33
<211> LENGTH: 18
<212> TYPE: DNA
<213> ORGANISM: Artificial
<220> FEATURE:
<223> OTHER INFORMATION: Part of delta F508 DNA with stopcodon at
      position 508
```

<400> SEQUENCE: 33
atcatctgat ttggtgtt                                                                                          18

<210> SEQ ID NO 34
<211> LENGTH: 45
<212> TYPE: RNA
<213> ORGANISM: Artificial
<220> FEATURE:
<223> OTHER INFORMATION: Part of delta F 508 RNA, with stopcodon at
      position 508

<400> SEQUENCE: 34
accauuaaag aaaauaucau cugauuuggu guuccuaug augaa                                                             45

<210> SEQ ID NO 35
<211> LENGTH: 7
<212> TYPE: PRT
<213> ORGANISM: Artificial
<220> FEATURE:
<223> OTHER INFORMATION: Part of CFTR WT polypeptide with stopcodon
      inserted at position 508

<400> SEQUENCE: 35

Thr Ile Lys Glu Asn Ile Ile
1               5

<210> SEQ ID NO 36
<211> LENGTH: 45
<212> TYPE: RNA
<213> ORGANISM: Artificial
<220> FEATURE:
<223> OTHER INFORMATION: Part of CFTR WT RNA with GA insertion

<400> SEQUENCE: 36
accauuaaag aaaauaucau cgauuuggug uuccuauga ugaau                                                             45

<210> SEQ ID NO 37
<211> LENGTH: 15
<212> TYPE: PRT
<213> ORGANISM: Artificial
<220> FEATURE:
<223> OTHER INFORMATION: Part of CFTR WT polypeptide with frameshift
      induced by GA insertion

<400> SEQUENCE: 37

Thr Ile Lys Glu Asn Ile Ile Asp Leu Val Phe Pro Met Met Asn
1               5                   10                  15

<210> SEQ ID NO 38
<211> LENGTH: 45
<212> TYPE: RNA
<213> ORGANISM: Artificial
<220> FEATURE:
<223> OTHER INFORMATION: Part of CFTR WT RNA with A insertion

<400> SEQUENCE: 38
accauuaaag aaaauaucau cauuuggugu uccuaugau gaaua                                                             45

<210> SEQ ID NO 39
<211> LENGTH: 12
<212> TYPE: PRT
<213> ORGANISM: Artificial
<220> FEATURE:
<223> OTHER INFORMATION: Part of CFTR WT polypeptide with frameshift
      induced stopcodon at position 513

```
<400> SEQUENCE: 39

Thr Ile Lys Glu Asn Ile Ile Ile Trp Cys Phe Leu
1               5                   10

<210> SEQ ID NO 40
<211> LENGTH: 18
<212> TYPE: DNA
<213> ORGANISM: Artificial
<220> FEATURE:
<223> OTHER INFORMATION: Part of CFTR DNA with Leucine codon inserted
      at codon position 508

<400> SEQUENCE: 40
atcatcctct ttggtgtt                                               18

<210> SEQ ID NO 41
<211> LENGTH: 45
<212> TYPE: RNA
<213> ORGANISM: Artificial
<220> FEATURE:
<223> OTHER INFORMATION: Part of the CFTR WT RNA with Leucine codon
      (CUC) insertion at position 508

<400> SEQUENCE: 41
accauuaaag aaaauaucau ccucuuuggu guuccuaug augaa                  45

<210> SEQ ID NO 42
<211> LENGTH: 15
<212> TYPE: PRT
<213> ORGANISM: Artificial
<220> FEATURE:
<223> OTHER INFORMATION: Part of CFTR WT polypeptide with Leucine
      inserted at position 508

<400> SEQUENCE: 42

Thr Ile Lys Glu Asn Ile Ile Leu Phe Gly Val Ser Tyr Asp Glu
1               5                   10                  15

<210> SEQ ID NO 43
<211> LENGTH: 45
<212> TYPE: RNA
<213> ORGANISM: Artificial
<220> FEATURE:
<223> OTHER INFORMATION: Part of CFTR WT RNA

<400> SEQUENCE: 43
auuucauucu guucucaguu uuccuggauu augccuggca ccauu                 45

<210> SEQ ID NO 44
<211> LENGTH: 15
<212> TYPE: PRT
<213> ORGANISM: Artificial
<220> FEATURE:
<223> OTHER INFORMATION: Part CFTR WT polypeptide

<400> SEQUENCE: 44

Ile Ser Phe Cys Ser Gln Phe Ser Trp Ile Met Pro Gly Thr Ile
1               5                   10                  15

<210> SEQ ID NO 45
<211> LENGTH: 45
<212> TYPE: RNA
<213> ORGANISM: Artificial
<220> FEATURE:
<223> OTHER INFORMATION: Part of CFTR WT RNA with stopcodon insertion
      at codon position 495
```

```
<400> SEQUENCE: 45
auuucauucu guucucaguu uugauccugg auuaugccug gcacc                    45

<210> SEQ ID NO 46
<211> LENGTH: 7
<212> TYPE: PRT
<213> ORGANISM: Artificial
<220> FEATURE:
<223> OTHER INFORMATION: Part of truncated CFTR WT polypeptide due to
      stopcodon inserted at position 495

<400> SEQUENCE: 46

Ile Ser Phe Cys Ser Gln Phe
1               5

<210> SEQ ID NO 47
<211> LENGTH: 48
<212> TYPE: RNA
<213> ORGANISM: Artificial
<220> FEATURE:
<223> OTHER INFORMATION: Part of CFTR WT RNA

<400> SEQUENCE: 47
uucuguucuc aguuuccug gauuaugccu ggcaccauua aagaaaau                  48

<210> SEQ ID NO 48
<211> LENGTH: 16
<212> TYPE: PRT
<213> ORGANISM: Artificial
<220> FEATURE:
<223> OTHER INFORMATION: Part of CFTR WT polypeptide

<400> SEQUENCE: 48

Phe Cys Ser Gln Phe Ser Trp Ile Met Pro Gly Thr Ile Lys Glu Asn
1               5                   10                  15

<210> SEQ ID NO 49
<211> LENGTH: 48
<212> TYPE: RNA
<213> ORGANISM: Artificial
<220> FEATURE:
<223> OTHER INFORMATION: Part of CFTR WT RNA with Leucine codon
      insertion at position 498

<400> SEQUENCE: 49
uucuguucuc aguuuccug gauccuuaug ccuggcacca uuaaagaa                  48

<210> SEQ ID NO 50
<211> LENGTH: 16
<212> TYPE: PRT
<213> ORGANISM: Artificial
<220> FEATURE:
<223> OTHER INFORMATION: Part of CFTR WT polypeptide with Leucine
      insertion at position 498

<400> SEQUENCE: 50

Phe Cys Ser Gln Phe Ser Trp Ile Leu Met Pro Gly Thr Ile Lys Glu
1               5                   10                  15

<210> SEQ ID NO 51
<211> LENGTH: 33
<212> TYPE: RNA
<213> ORGANISM: Artificial
<220> FEATURE:
<223> OTHER INFORMATION: Oligonucleotide CFTR-R117

<400> SEQUENCE: 51
```

-continued

```
auaaaucgcg auagagcguu ccuccuuguu auc                         33
```

<210> SEQ ID NO 52
<211> LENGTH: 45
<212> TYPE: RNA
<213> ORGANISM: Artificial
<220> FEATURE:
<223> OTHER INFORMATION: Part of 117H RNA

<400> SEQUENCE: 52

```
gacccggaua acaaggagga acacucuauc gcgauuuauc uaggc            45
```

<210> SEQ ID NO 53
<211> LENGTH: 15
<212> TYPE: PRT
<213> ORGANISM: Artificial
<220> FEATURE:
<223> OTHER INFORMATION: Part of 117H polypeptide

<400> SEQUENCE: 53

```
Asp Pro Asp Asn Lys Glu Glu His Ser Ile Ala Ile Tyr Leu Gly
1               5                   10                  15
```

<210> SEQ ID NO 54
<211> LENGTH: 45
<212> TYPE: RNA
<213> ORGANISM: Artificial
<220> FEATURE:
<223> OTHER INFORMATION: Part of CFTR WT RNA

<400> SEQUENCE: 54

```
gacccggaua acaaggagga acgcucuauc gcgauuuauc uaggc            45
```

<210> SEQ ID NO 55
<211> LENGTH: 15
<212> TYPE: PRT
<213> ORGANISM: Artificial
<220> FEATURE:
<223> OTHER INFORMATION: Part of CFTR WT polypeptide

<400> SEQUENCE: 55

```
Asp Pro Asp Asn Lys Glu Glu Arg Ser Ile Ala Ile Tyr Leu Gly
1               5                   10                  15
```

<210> SEQ ID NO 56
<211> LENGTH: 33
<212> TYPE: RNA
<213> ORGANISM: Artificial
<220> FEATURE:
<223> OTHER INFORMATION: oligonucleotide CFTR-G542

<400> SEQUENCE: 56

```
gugauuccac cuucuccaag aacuauauug ucu                         33
```

<210> SEQ ID NO 57
<211> LENGTH: 45
<212> TYPE: RNA
<213> ORGANISM: Artificial
<220> FEATURE:
<223> OTHER INFORMATION: Part of 542X RNA

<400> SEQUENCE: 57

```
gagaaagaca auauaguucu uugagaaggu ggaaucacac ugagu            45
```

<210> SEQ ID NO 58

```
<211> LENGTH: 7
<212> TYPE: PRT
<213> ORGANISM: Artificial
<220> FEATURE:
<223> OTHER INFORMATION: Part of 542X truncated polypeptide

<400> SEQUENCE: 58

Glu Lys Asp Asn Ile Val Leu
1               5

<210> SEQ ID NO 59
<211> LENGTH: 45
<212> TYPE: RNA
<213> ORGANISM: Artificial
<220> FEATURE:
<223> OTHER INFORMATION: Part of CFTR WT RNA

<400> SEQUENCE: 59
gagaaagaca auauaguucu uggagaaggu ggaaucacac ugagu            45

<210> SEQ ID NO 60
<211> LENGTH: 15
<212> TYPE: PRT
<213> ORGANISM: Artificial
<220> FEATURE:
<223> OTHER INFORMATION: Part of CFTR WT polypeptide

<400> SEQUENCE: 60

Glu Lys Asp Asn Ile Val Leu Gly Glu Gly Gly Ile Thr Leu Ser
1               5                   10                  15

<210> SEQ ID NO 61
<211> LENGTH: 33
<212> TYPE: RNA
<213> ORGANISM: Artificial
<220> FEATURE:
<223> OTHER INFORMATION: oligonucleotide CFTR-W1282

<400> SEQUENCE: 61
cuccaaaggc uuccuccac uguugcaaag uua                          33

<210> SEQ ID NO 62
<211> LENGTH: 45
<212> TYPE: RNA
<213> ORGANISM: Artificial
<220> FEATURE:
<223> OTHER INFORMATION: Part of 1282X RNA

<400> SEQUENCE: 62
gauucaauaa cuuugcaaca gugaaggaaa gccuuggag ugaua             45

<210> SEQ ID NO 63
<211> LENGTH: 7
<212> TYPE: PRT
<213> ORGANISM: Artificial
<220> FEATURE:
<223> OTHER INFORMATION: Part of 1282X truncated polypeptide

<400> SEQUENCE: 63

Asp Ser Ile Thr Leu Gln Gln
1               5

<210> SEQ ID NO 64
<211> LENGTH: 45
<212> TYPE: RNA
<213> ORGANISM: Artificial
<220> FEATURE:
```

```
<223> OTHER INFORMATION: Part of CFTR WT RNA

<400> SEQUENCE: 64
gauucaauaa cuuugcaaca guggaggaaa gccuuuggag ugaua          45

<210> SEQ ID NO 65
<211> LENGTH: 15
<212> TYPE: PRT
<213> ORGANISM: Artificial
<220> FEATURE:
<223> OTHER INFORMATION: Part of CFTR WT polypeptide

<400> SEQUENCE: 65

Asp Ser Ile Thr Leu Gln Gln Trp Arg Lys Ala Phe Gly Val Ile
1               5                   10                  15

<210> SEQ ID NO 66
<211> LENGTH: 33
<212> TYPE: RNA
<213> ORGANISM: Artificial
<220> FEATURE:
<223> OTHER INFORMATION: oligonucleotide CFTR-N1303

<400> SEQUENCE: 66
guucauaggg auccaaguuu uuucuaaaug uuc          33

<210> SEQ ID NO 67
<211> LENGTH: 45
<212> TYPE: RNA
<213> ORGANISM: Artificial
<220> FEATURE:
<223> OTHER INFORMATION: Part of 1303K RNA

<400> SEQUENCE: 67
uuuucuggaa cauuuagaaa aaaguuggau cccuaugaac agugg          45

<210> SEQ ID NO 68
<211> LENGTH: 15
<212> TYPE: PRT
<213> ORGANISM: Artificial
<220> FEATURE:
<223> OTHER INFORMATION: Part of 1303K PP

<400> SEQUENCE: 68

Phe Ser Gly Thr Phe Arg Lys Lys Leu Asp Pro Tyr Glu Gln Trp
1               5                   10                  15

<210> SEQ ID NO 69
<211> LENGTH: 45
<212> TYPE: RNA
<213> ORGANISM: Artificial
<220> FEATURE:
<223> OTHER INFORMATION: Part of CFTR WT RNA

<400> SEQUENCE: 69
uuuucuggaa cauuuagaaa aaacuuggau cccuaugaac agugg          45

<210> SEQ ID NO 70
<211> LENGTH: 15
<212> TYPE: PRT
<213> ORGANISM: Artificial
<220> FEATURE:
<223> OTHER INFORMATION: Part of CFTR WT polypeptide

<400> SEQUENCE: 70

Phe Ser Gly Thr Phe Arg Lys Asn Leu Asp Pro Tyr Glu Gln Trp
1               5                   10                  15
```